(12) United States Patent
Koide et al.

(10) Patent No.: US 9,771,377 B2
(45) Date of Patent: Sep. 26, 2017

(54) SYNTHESIS OF FR901464 AND ANALOGS WITH ANTITUMOR ACTIVITY

(71) Applicant: University of Pittsburgh—Of the Commonwealth System of Higher Education, Pittsburgh, PA (US)

(72) Inventors: Kazunori Koide, Pittsburgh, PA (US); Sami Saif Eldin Ali Osman, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/654,305

(22) PCT Filed: Dec. 19, 2013

(86) PCT No.: PCT/US2013/076454
§ 371 (c)(1),
(2) Date: Jun. 19, 2015

(87) PCT Pub. No.: WO2014/100367
PCT Pub. Date: Jun. 26, 2014

(65) Prior Publication Data
US 2015/0307512 A1    Oct. 29, 2015

Related U.S. Application Data

(60) Provisional application No. 61/745,148, filed on Dec. 21, 2012.

(51) Int. Cl.
| | |
|---|---|
| *C07D 493/10* | (2006.01) |
| *C07D 413/14* | (2006.01) |
| *C07D 413/12* | (2006.01) |
| *C07C 49/603* | (2006.01) |
| *C07D 309/30* | (2006.01) |
| *C07D 407/06* | (2006.01) |
| *C07D 493/04* | (2006.01) |

(52) U.S. Cl.
CPC .......... *C07D 493/10* (2013.01); *C07C 49/603* (2013.01); *C07D 309/30* (2013.01); *C07D 407/06* (2013.01); *C07D 413/12* (2013.01); *C07D 413/14* (2013.01); *C07D 493/04* (2013.01)

(58) Field of Classification Search
None
See application file for complete search history.

(56) References Cited

U.S. PATENT DOCUMENTS

| | | | |
|---|---|---|---|
| 5,010,176 A | 4/1991 | Barton | |
| 5,156,840 A | 10/1992 | Goers et al. | |
| 5,272,253 A | 12/1993 | Koppel et al. | |
| 5,514,794 A | 5/1996 | Barton | |
| 5,607,915 A | 3/1997 | Patton | |
| 5,643,573 A | 7/1997 | Barton et al. | |
| 5,665,358 A | 9/1997 | Barton et al. | |
| 5,795,560 A | 8/1998 | Reed | |
| 7,825,267 B2 | 11/2010 | Koide et al. | |
| 8,309,599 B2 | 11/2012 | Koide | |
| 2005/0276812 A1 | 12/2005 | Ebens et al. | |

FOREIGN PATENT DOCUMENTS

WO    2009031999    *    3/2009

OTHER PUBLICATIONS

"Cancer Prevention Overview—National Cancer Institute", http://www.cancer.gov/cancertopics/pdq/prevention/overview/patient, accessed Apr. 9, 2010.*
Osman. MedChemComm, 2011, 2, 38-43, available online Nov. 2, 2010.*
Satchi-Fairano (Advanced Polymer Science, 2006, 193, 1-65.*
International Search Report and Written Opinion issued in International Patent Application No. PCT/US2013/076454, completed Apr. 22, 2014.
International Search Report and Written Opinion issued in related International Patent Application No. PCT/US2007/019550, dated Jul. 3, 2008.
Nakajima et al., "New antitumor substances, FR901463, FR901464, FR901465, II. Activities against experimental tumors in mice and mechanism of action," Journ. of Antibiotics, vol. 49, No. 12, pp. 1204-1211 (1996), [Abstract].
International Preliminary Report on Patentability issued in related International Patent Application No. PCT/US2013/076454, dated Jun. 23, 2015.
Andreas Vogt et al., "A Scalable High-Content Cytotoxicity Assay Insensitive to Changes in Mitochondrial Metabolic Activity", Oncology Research, vol. 14, No. 6, 2004,pp. 305-314.
Ari M.P. Koskinen et al., "A new Access to Enantiomerically Pure Deoxy Aminohexoses: Methyl 4-Amino-4,6-Dideoxygulopyranoside and epi-Tolyposamine", Tetrahedron. vol. 53, No. 18, pp. 6473-6484, 1997.
Charlotte F. McDonagh et al., "Engineered antibody-drug conjugates with defined sites and stoichiometries of drug attachment", Protein Engineering Design & Selection, vol. 19, No. 7, pp. 299-307, 2006.
Christopher F. Thompson et al., "FR901494: Total Synthesis, Proof of Structure, and Evaluation of Synthetic Analogues", J. Am. Chem. Soc. 2001, 123, 9974-9983.
Christopher F. Thompson et al., "Total Synthesis of FR901464. Convergent Assembly of Chiral Components Prepared by Asymmetric Catalysis", J. Am. Chem. Soc. 2000, 122, 10482-10483.
Christopher T. Meta et al., "Trans-Selective Conversions of γ-Hydroxy-α,β-Alkynoic Esters to ?-Hydroxy-α,β-Alenoic Esters", Organic Letters, vol. 6, No. 11, 1785-1787, 2004.
D. Lansing Taylor et al., "Real-time molecular and cellular analysis: the new frontier of drug discovery", Current Opinion in Biotechnology, 2001, 12:75-81.

(Continued)

Primary Examiner — Noble Jarrell
(74) Attorney, Agent, or Firm — Foley & Lardner LLP

(57) ABSTRACT

The present invention provides novel analogs of FR901464, as well as an improved methodology for preparing FR901464 and its analogs. These compounds display an anti-cancer activity and are candidates for therapies against a number of disease states associated with dysfunctional RNA splicing.

27 Claims, 2 Drawing Sheets

(56) References Cited

OTHER PUBLICATIONS

Daisuke Kaida et al., "Spliceostatin A targets SF3b and inhibits both splicing and nuclear retention of pre-mRNA", Nature Chemical Biology, vol. 3, No. 9, Sep. 2007, pp. 576-583.
Hidenori Nakajima et al., "New Antitumor Substances, FR901463, FR901464 and FR901465", The Journal of Antibiotics, vol. 50, No. 1, Jan. 1997, pp. 96-99.
Hiroki Suzuki et al., "Epidermal Growth Factor Receptor Tyrosine Kinase Inhibition Augments a Murine Model of Pulmonary Fibrosis", Cancer Research 63m 5054-5059, Aug. 2003.
Kathleen W. Scotto et al., "Amplification and Expression of Genes Associated with Multidrug Resistance in Mammalian Cells", Science vol. 232, May 1986, pp. 751-755.
Kenneth A. Giuliano et al., "High-Content Screening: A New Approach to Easing Key Bottlenecks in the Drug Discovery Process", Journal of Biomolecular Screening, vol. 2, No. 4, 1997, pp. 249-259.
Lata Dusre et al., "DNA Damage, Cytotoxicity and Free Radical Formation by Mitomycin C in Human Cells", Chem. Biol. Interactions, 71, (1989) 63-78.
Leo A. Paquette et al., "A Convenient Method for Removing All Highly-Colored Byproducts Generated during Olefin Metathesis Reactions", Organic Letters, vol. 2, No. 9, 2000, pp. 1259-1261.
Leonard C. Erickson et al., "DNA crosslinking and cytotoxicity in normal and transformed human cells treated with antitumor nitrosoureas", Proc. Natl. Acad. Sci. USA, vol. 77. No. 1, pp. 467-471, Jan. 1980.
Peter Wipf et al., "Cellular Analysis of Disorazole C1 and Structure-Activity Relationship of Analogs of the Natural Product", Chem. Biol. Drug. Des. 2006, 67:66-73.
Richard C. Larock et al.., "Mercury in Organic Chemistry. 24.1-Mercuration and Subsequent Carbonylation of 4-Hydroxy-2-alkyn-1-ones: A Novel Route to Furans", J. Org. Chem. 1983, 48, 2151-2158.
Robert H.F. Peterson et al., "Alteration of Plasma Membrane Glycopeptides and Gangliosides of Chinese Hamster Cells Accompanying Development of Resistance to Daunorubicin and Vincristine", Cancer Research, 43, Jan. 1983, 222-228.
Roderick W. Bates et al., "Assessment of Butene-1,4-Diols as Starting Materials for the Preparation of p-Allyltricarbonyliron Complexes", Tetrahedron vol. 46, No. 11, pp. 4063-4082, 1990.

Shatrughan P. Shahi et al., "A Mild Method for the preparation of γ-Hydroxy-α,β-Acetylenic Esters", Angew. Chem. Int. Ed. 2004, 43, 2525-2527.
Tian-Jye Hsieh et al., "Liriodenine inhibits the proliferation of human hepatoma cell lines by blocking cell cycle progression and nitric oxide-mediated activation of p53 expression", Food and Chemical Toxicology 43 (2005) 1117-1126.
W.W. Nichols et al., "Characterization of a New Human Diploid Cell Strain, IMR-90", Science, vol. 196, Apr. 1977, pp. 60-63.
Yutaka Nakamura et al., "Dehydrooligopeptides. XVII. Practical Synthesis of All of the Diastereomers of N,N-Protected 2,3-Diaminobutanoic Acids from L- and D-Threonine Derivatives", Bull. Chem. Soc. Jpn. 68, 1369-1377 (1995).
Zhiyong Wang et al. "Structure-activity and High-content Imaging Analyses of Novel Tubulysins", Chem Biol Drug Des 2007; 70:75-86.
Masato Horigome et al., A Synthesis of FR901464, Tetrahedron Letters 42, pp. 8207-8210 (2001).
Gill, et al., "A Modular Platform for the Rapid Site-Specific Radiolabeling of Proteins with $^{18}$F Exemplified by Quantitative Positron Emission Tomography of Human Epidermal Growth Factor Receptor 2," J. Med. Chem, vol. 52, No. 19, pp. 5816-5825 (2009).
Albert, et al., Total Syntheses, Fragmentation Studies, and Antitumor/Antiproliferative Activities of FR901464 and Its Low Picomolar Analogue, J. Am. Chem. Soc., vol. 129, pp. 2648-2659 (2007).
Ryohei Furumi et al, Spliceostatin a blocks angiogenesis by inhibiting global gene expression including VEGF, Cancer science 2010 vol. 101, pp. 2483-2489.
Sarah Muller et al., "Synthesis of a Pladienolide B Analogue with the Fully Functionalized Core Structure," Organic Letters, 2011, vol. 13, pp. 3940-3943 [Abstract].
Yang Gao, Comparison of splicing factor 3b inhibitors in human cells, Chennbiochem, Jan. 2, 2013;14(1)49-52. doi: 10.1002/cibc.201200558. E.pub Nov. 22, 2012 [Abstract].
Non-Final Office Action U.S. Appl. No. 11/852,278 dated Dec. 18, 2009.
Osman et al., "Structural Requirements for the Antiproliferative Activity of Pre-mRNA Splicing Inhibitor FR901464," vol. 17, No. 3, pp. 895-904 (2011) [Abstract].

\* cited by examiner

SYNTHESIS OF FR901464 AND ANALOGS WITH ANTITUMOR ACTIVITY

CROSS-REFERENCE TO RELATED APPLICATIONS

This application is the national stage entry under 35 USC §371 of International Patent Application No. PCT/US2013/076454, filed on Dec. 19, 2013, which claims priority to U.S. Provisional Patent Application No. 61/745,148, filed on Dec. 21, 2012. The contents of these applications are incorporated herein by reference in their entirety.

STATEMENT OF GOVERNMENT FUNDING

This invention was made with government support under grant number CA120792 awarded by the National Institute of Health. The government has certain rights in the invention.

BACKGROUND OF THE INVENTION

The natural product FR901464, isolated from the broth of a *Pseudomonas* sp. No. 2663 culture, is a transcriptional activator. It lowers the mRNA levels of p53, p21, c-myc, and E2F-1 in MCF-7 cells at 20 nM, and it induces apparent apoptosis in MCF-7 cells with the impressive LC50 of 0.5 nM. FR901464 also exhibits an antitumor activity in a mouse model at remarkably low concentrations (0.056-0.18 mg/kg).

This pharmacological profile for FR901464 has drawn considerable interest, focusing on its potential as an anticancer agent. A 4-TEGylated-FR901464 analog, depicted below, has been prepared and found to have a high cancer cell antiproliferative activity.

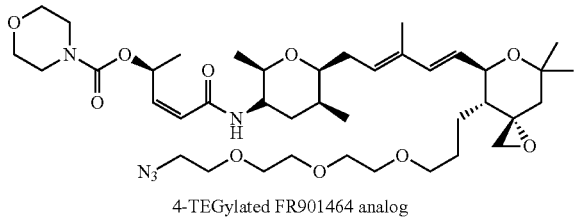

4-TEGylated FR901464 analog

Additionally, the right fragment of the 4-TEGylated-FR901464 analog, depicted below, was found to exhibit high cancer cell antiproliferative activity.

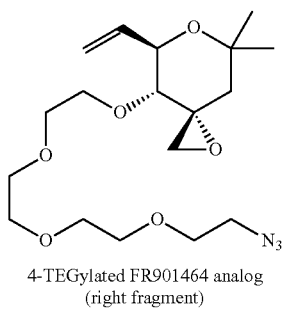 [SMILES: C=C[C@H]1OC(C)(C)C[C@@]2(CO2)[C@@H]1OCCOCCOCCOCCN=[N+]=[N-]]

4-TEGylated FR901464 analog
(right fragment)

The preparation of more potent analogs has been limited by a lengthy synthesis involving at least nineteen linear steps and typically forty or more in total. Accordingly, the present invention provides novel analogs of FR901464, as well as new and improved methods for preparing FR901464 and its analogs.

SUMMARY OF THE INVENTION

The present invention relates to compounds and pharmaceutical compositions containing them, to their preparation, to intermediates useful in their preparation, and to uses for the compounds, primarily but not exclusively in treating cancer. In one embodiment of the invention, a compound, stereoisomer, or pharmaceutically acceptable salt or ester thereof is provided that conforms to Formula (I):

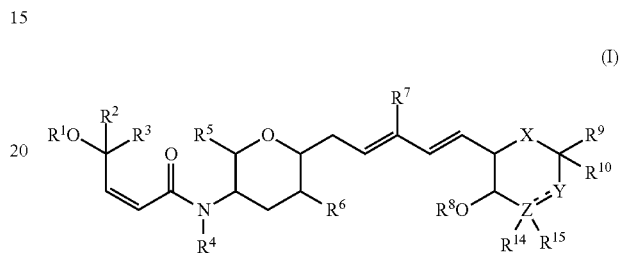

wherein
X is selected from the group consisting of O and $C(R^{11})_2$;
Y is selected from the group consisting of C, CH, $C(R^{11})_2$ and O;
Z is selected from the group consisting of C and CH;
⁓ represents a single or a double bond between Y and Z;
$R^1$ is selected from the group consisting of H, $C_{1-6}$-alkyl, halo($C_{1-6}$-alkyl), $C(O)R^{11}$, $C(O)OR^{11}$, and $C(O)NR^{12}R^{13}$,
wherein $R^{11}$ is H, $C_{1-6}$-alkyl, or halo($C_{1-6}$-alkyl), and wherein $R^{12}$ and $R^{13}$ are independently selected from the group consisting of H, $C_{1-6}$-alkyl, and halo($C_{1-6}$-alkyl);
or $R^{12}$ and $R^{13}$, together with the nitrogen atom to which they are bound, form a heterocyclic or heteroaromatic ring;
$R^2$, $R^3$, $R^4$, $R^5$, and $R^6$ are independently selected from the group consisting of H, $C_{1-6}$-alkyl, and halo($C_{1-6}$-alkyl);
$R^7$ is selected from the group consisting of H, $C_{1-6}$-alkyl and halo($C_{1-6}$-alkyl);
$R^8$ is selected from the group consisting of an optionally substituted polyethylene moiety and H;
$R^9$ and $R^{10}$ are independently selected from the group consisting of H, $C_{1-6}$-alkyl, and $C_{1-6}$-alkyl substituted with one to three groups independently selected from halo, hydroxy, and $C_{1-6}$-alkoxy;
or $R^9$ and $R^{10}$, together with the carbon atom to which they are bound, form a carbonyl group;
$R^{14}$ and $R^{15}$ are independently selected from the group consisting of hydrogen, halo($C_{1-6}$-alkyl), $C(O)R^{11}$, F, Cl, $NO_2$, and $B(OR^{11})_2$, wherein at least one of $R^{14}$ and $R^{15}$ is other than hydrogen when ⁓ represents a single bond, and wherein $R^{11}$ is as defined above;
or $R^{14}$ and $R^{15}$, together with the carbon atom to which they are bound, form an epoxide ring or a carbonyl group;
or $R^{14}$ and $R^{15}$ together represent a substituent selected from the group consisting of =$NHNH_2$ and =NOH;
or $R^8$, $R^{14}$, and $R^{15}$ together with the carbon atoms to which they are bound, represent the following structure:

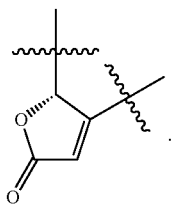 [SMILES: *C1=CC(=O)O[C@@H]1*]

According to another embodiment of the invention, a compound, stereoisomer, or pharmaceutically acceptable salt or ester thereof is provided that conforms to Formula (II):

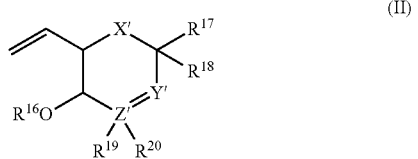

wherein
- X' is selected from the group consisting of O and $C(R^{22})_2$; wherein $R^{22}$ is H, $C_{1-6}$-alkyl, or halo($C_{1-6}$-alkyl); and
- Y' is selected from the group consisting of C, CH, $C(R^{22})_2$ and O;
- Z' is selected from the group consisting of C and CH;
- ⟿ represents a single or a double bond between Y' and Z';
- $R^{16}$ is selected from the group consisting of H, an optionally substituted polyethylene glycol moiety and H;
- $R^{17}$ and $R^{18}$ are independently selected from the group consisting of H, $C_{1-6}$-alkyl, and $C_{1-6}$-alkyl substituted with one to three groups independently selected from halo, hydroxy, and $C_{1-6}$-alkoxy;
- or $R^{17}$ and $R^{18}$, together with the carbon atom to which they are bound, form a carbonyl group;
- $R^{19}$ and $R^{20}$ are independently selected from the group consisting of hydrogen, halo($C_{1-6}$-alkyl), $C(O)R^{22}$, F, Cl, $NO_2$, and $B(OR^{22})_2$, wherein at least one of $R^{19}$ and $R^{20}$ is other than hydrogen when ⟿ represents a single bond, and wherein $R^{22}$ is as defined above;
- or $R^{19}$ and $R^{20}$, together with the carbon atom to which they are bound, form an epoxide ring or a carbonyl group;
- or $R^{19}$ and $R^{20}$ together represent a substituent selected from the group consisting of =$NHNH_2$ and =NOH;
- or $R^{16}$, $R^{19}$, and $R^{20}$ together with the carbon atoms to which they are bound, represent the following structure:

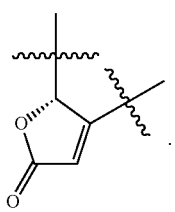 [SMILES: *C1=CC(=O)O[C@@H]1*]

In another embodiment, the invention provides a process for preparing a compound, stereoisomer, or pharmaceutically acceptable salt or ester thereof having Formula (Ia):

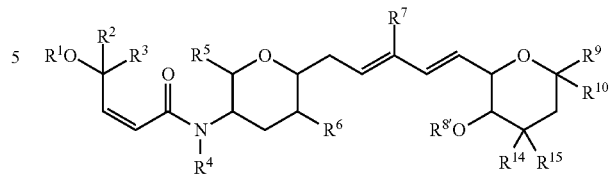

where
- $R^1$ is selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$,
  wherein each $R^{11}$ is independently H, $C_{1-6}$-alkyl, or halo($C_{1-6}$-alkyl), and
  wherein $R^{12}$ and $R^{13}$ are independently selected from the group consisting of H, $C_{1-6}$-alkyl, and halo($C_{1-6}$-alkyl);
  or $R^{12}$ and $R^{13}$, together with the nitrogen atom to which they are bound, form a heterocyclic or heteroaromatic ring;
- $R^2$, $R^3$, $R^4$, $R^5$, and $R^6$ are independently selected from the group consisting of H, $C_{1-6}$-alkyl, and halo($C_{1-6}$-alkyl);
- $R^7$ is selected from the group consisting of H, $C_{1-6}$-alkyl and halo($C_{1-6}$-alkyl); and
- $R^{8'}$ is H or an optionally substituted polyethylene glycol moiety, and
- $R^9$ and $R^{10}$ are independently selected from the group consisting of H, $C_{1-6}$-alkyl, and $C_{1-6}$-alkyl substituted with one to three groups independently selected from halo, hydroxy, $C_{1-6}$-alkoxy, and OPg;
- $R^{14}$ or $R^{15}$ are independently selected from the group consisting of hydrogen, halo($C_{1-6}$-alkyl), $C(O)R^{11}$, F, Cl, $NO_2$, and $B(OR^{11})_2$, wherein at least one of $R^{14}$ and $R^{15}$ is other than hydrogen, and wherein $R^{11}$ is as defined above; and
- each Pg is independently a hydroxy protecting group;

said method comprising the steps of
(A) contacting a compound of Formula (III):

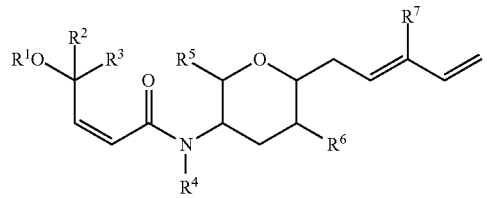

wherein $R^1$, $R^2$, $R^3$, $R^4$, $R^5$, $R^6$, and $R^7$ are as defined above with a compound of Formula (IIa):

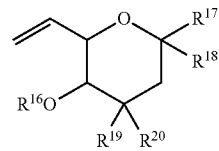

wherein $R^{16}$ is hydrogen and $R^{17}$, $R^{18}$, $R^{19}$, and $R^{20}$ are as defined above, in the presence of an olefin metathesis catalyst;
and if $R^8$ is an optionally substituted polyethylene glycol moiety, then the method further comprises
(B) contacting the product of step (A) with a compound of the formula (IV)

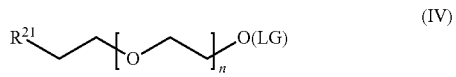

(IV)

wherein
$R^{21}$ is selected from the group consisting of azide, tetrazole and triazole with hydrogen, alkyl, or substituted alkyl substituents;
n is an integer selected from 1, 2, 3, 4, 5, and 6; and
LG is a leaving group.

DETAILED DESCRIPTION

Definitions

Figure 1:
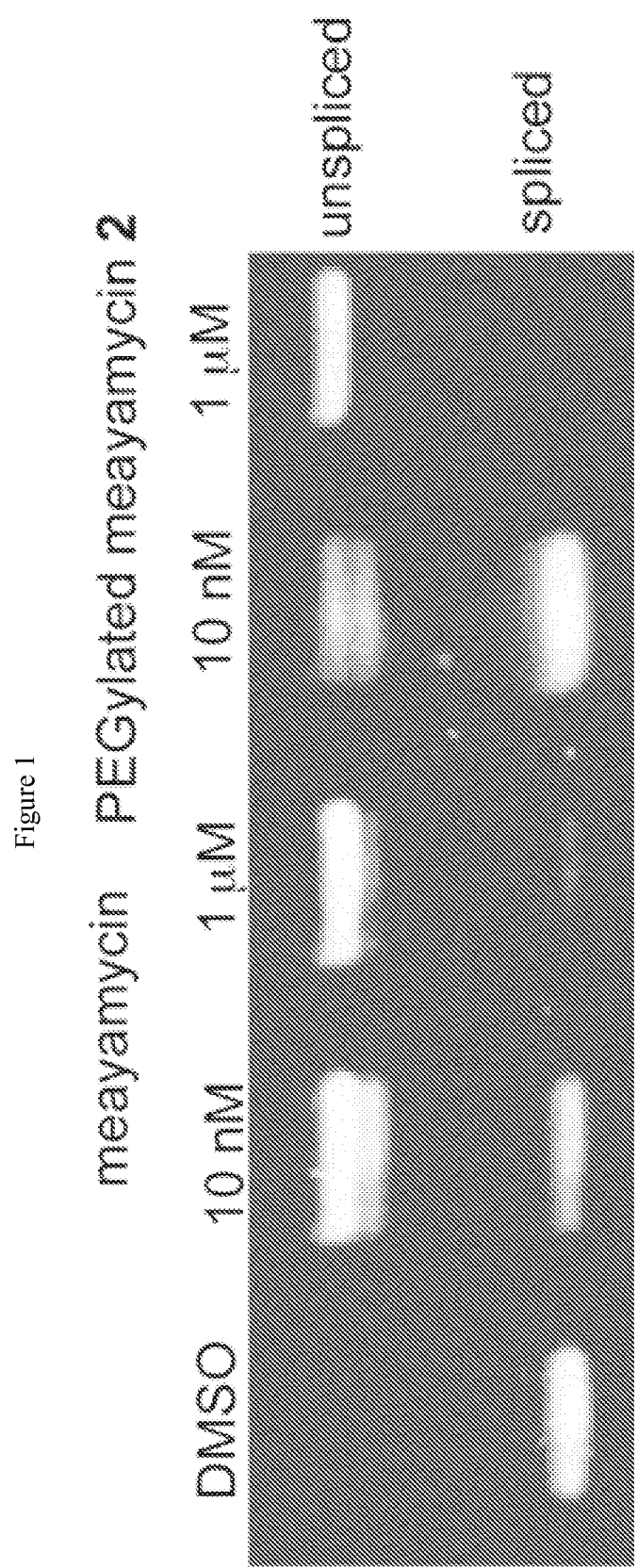
FIG. 1 shows RT-PCR analysis of total RNA extracted from 4-TEGylated meayamycin-, meayamycin-, and DMSO-treated HEK-293-II cells.

It is to be understood that the terminology used herein is for the purpose of describing particular embodiments only and is not intended to limit the scope of the present invention. The following definitions shall apply unless otherwise indicated.

The phrase "cellular proliferative disorder" refers to a disease or pathology that is characterized by abnormal, uncontrolled cell division. Exemplary of such disorders and pathologies are neoplasia, including cancers, hyperplasias such as endometrial hyperplasia and benign prostatic hyperplasia, restenosis, cardiac hypertrophy, immune disorders characterized, for example, by a dysfunctional proliferation response of the cellular immune system, and inflammation. Illustrative cancers in this regard are acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

"$C_{1-6}$-alkyl" refers to monovalent saturated aliphatic hydrocarbyl groups having from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH_2$—), sec-butyl (($CH_3$)($CH_3CH_2$)CH—), t-butyl (($CH_3)_3$C—), n-pentyl ($CH_3CH_2CH_2CH_2CH_2$—), and neopentyl (($CH_3)_3CCH_2$—).

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl.

The term "heterocycle" or "heterocycloalkyl" as used herein refers to 5- to 14-membered ring systems, such as 5- to 6-membered ring systems, which are either saturated, unsaturated, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles may be monocyclic, bicyclic, or tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl.

"Hydroxy" refers to the group —OH.

"Hydroxy protecting group" refers to protecting groups for an OH group. Suitable hydroxy protecting groups as well as suitable conditions for protecting and deprotecting particular functional groups are well known in the art. For example, numerous such protecting groups are described in T. W. Greene and P. G. M. Wuts, PROTECTING GROUPS IN ORGANIC SYNTHESIS, 3$^{rd}$ ed., Wiley, New York. Such hydroxy protecting groups include $C_{1-6}$ alkyl ethers, benzyl ethers, p-methoxybenzyl ethers, silyl ethers, and the like.

"$C_{1-6}$-alkoxy" refers to the group —O—($C_{1-6}$-alkyl) wherein $C_{1-6}$-alkyl is defined herein. $C_{1-6}$-alkoxy includes, by way of example, methoxy, ethoxy, n-propoxy, isopropoxy, n-butoxy, t-butoxy, sec-butoxy, and n-pentoxy.

"Subject" refers to mammals and includes humans and non-human mammals.

"Pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Stereoisomer" or "stereoisomers" refer to compounds that differ in the chirality of one or more stereocenters. Stereoisomers include enantiomers, diastereomers, and racemates.

"Treating" or "treatment" of a disease in a subject refers to (1) preventing the disease from occurring in a subject that is predisposed or does not yet display symptoms of the disease; (2) inhibiting the disease or arresting its development; or (3) ameliorating or causing regression of the disease.

Compounds

The present invention provides a compound, stereoisomer, or pharmaceutically acceptable salt or ester thereof having Formula I as described generally hereinabove:

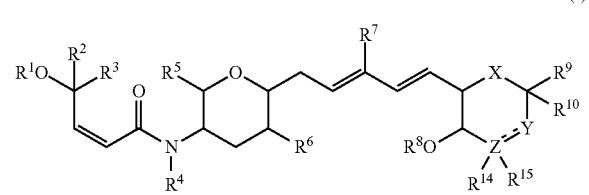

(I)

wherein X, Y, Z, $R^1$, $R^2$, $R^3$, $R^4$, $R^5$, $R^6$, $R^7$, $R^9$, $R^{10}$, $R^{14}$ and $R^{15}$ are as previously defined.

In one embodiment, provided is a compound having formula (Ia):

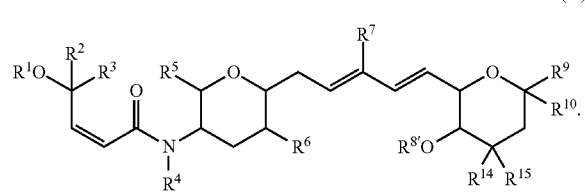

(Ia)

wherein $R^1$, $R^2$, $R^3$, $R^4$, $R^5$, $R^6$, and $R^7$ are as previously defined, and wherein $R^8$ is an optionally substituted polyethylene glycol moiety, and $R^9$ and $R^{10}$ are independently selected from the group consisting of H, $C_{1-6}$-alkyl, and $C_{1-6}$-alkyl substituted with one to three groups independently selected from halo, hydroxy, and $C_{1-6}$-alkoxy, and $R^{14}$ and $R^{15}$ are independently selected from the group consisting of hydrogen, halo($C_{1-6}$-alkyl), $C(O)R^{11}$, F, Cl, $NO_2$, and $B(OR^{11})_2$, wherein at least one of $R^{14}$ and $R^{15}$ is other than hydrogen, and wherein $R^{11}$ is as defined above;

or $R^{14}$ and $R^{15}$, together with the carbon atom to which they are bound, form an epoxide ring or a carbonyl group.

In one embodiment, provided is a compound having Formula (Ib):

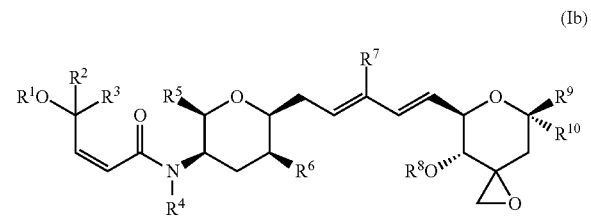

(Ib)

wherein $R^1$, $R^2$, $R^3$, $R^4$, $R^5$, $R^6$, $R^7$, $R^8$, $R^9$, and $R^{16}$ are as previously defined in Formula (Ia).

In another embodiment, the invention provides a compound having Formula (Ic):

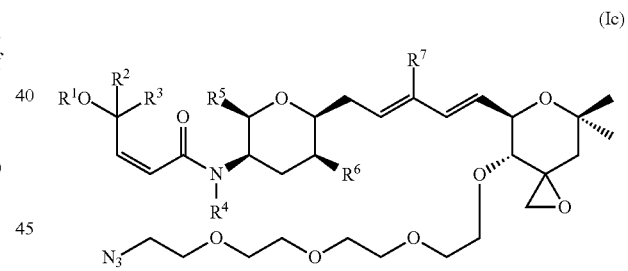

(Ic)

wherein $R^1$, $R^2$, $R^3$, $R^4$, $R^5$, $R^6$, and $R^7$ are as previously defined.

In one embodiment, provided is a compound having Formula (Id):

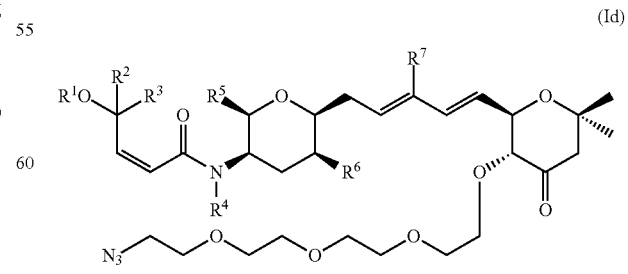

(Id)

wherein $R^1$, $R^2$, $R^3$, $R^4$, $R^5$, $R^6$, and $R^7$ are as previously defined.

In some embodiments, $R^1$ is $C(O)R^{11}$ and $R^{11}$ is $C_{1-6}$-alkyl or halo($C_{1-6}$-alkyl). For instance, in some embodiments $R^1$ is $C(O)CH_3$.

In other embodiments, at least one of $R^2$, $R^3$, $R^5$, and $R^6$ is $C_{1-6}$-alkyl. To illustrate, one embodiment provides compounds wherein at least one of $R^2$, $R^3$, $R^5$, and $R^6$ is $CH_3$. In some embodiments, each of $R^3$ and $R^5$ is $CH_3$.

In some embodiments, $R^2$ is hydrogen. Similarly, $R^4$ and $R^6$ can be independently hydrogen.

In still other embodiments, $R^7$ is $CH_3$ or $CF_3$

In some embodiments, at least one of $R^9$ and $R^{10}$ is selected from the group consisting of $C_{1-6}$-alkyl and $C_{1-6}$-alkyl substituted with one to three groups independently selected from halo, hydroxy, and $C_{1-6}$-alkoxy. In other embodiments, at least one of $R^9$ and $R^{10}$ is independently selected from the group consisting of $CH_3$, $CH_2I$, and $CH_2OH$. In other embodiments, each of $R^9$ and $R^{10}$ is methyl.

In some embodiments $R^{14}$ or $R^{15}$, taken together with the carbon atom to which they are both bound, form a carbonyl group. In some embodiments $R^{14}$ or $R^{15}$, taken together with the carbon atom to which they are both bound, form a epoxide ring.

In some embodiments, $R^8$, $R^{14}$, and $R^{15}$ together with the carbon atoms to which they are bound, represent the following structure:

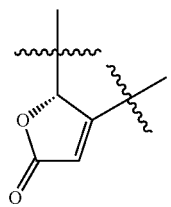

Exemplary compounds of the present invention include:

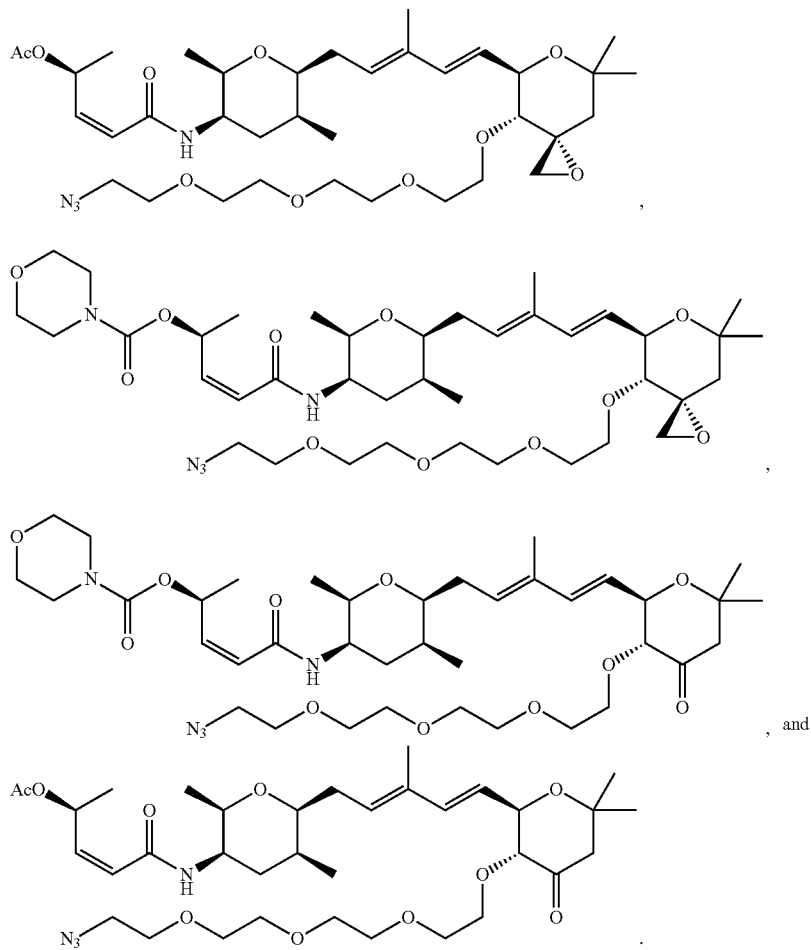

In some embodiments, a compound of the present invention according to a formula described herein features, in relevant part, a cyclic moiety as shown below:

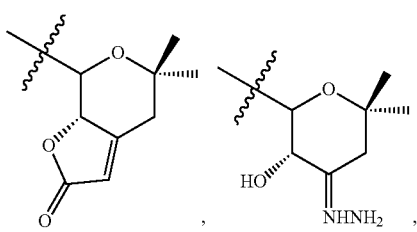

-continued

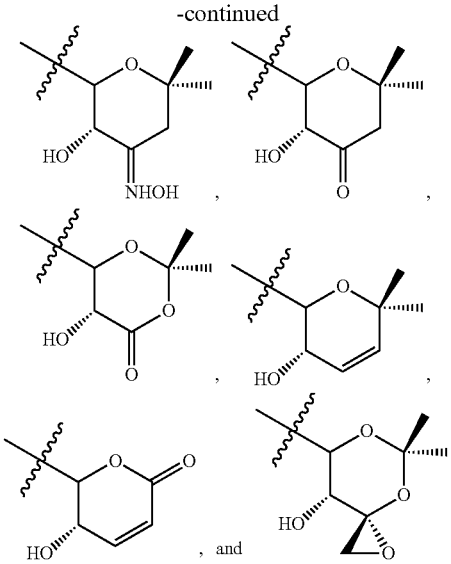

The present invention provides also a compound, stereoisomer, or pharmaceutically acceptable salt or ester thereof having Formula (II) as described generally hereinabove:

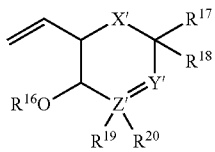
(II)

wherein X', Y', Z', $R^{16}$, $R^{17}$, $R^{18}$, $R^{19}$, and $R^{20}$ are as previously defined.

According to another embodiment of the invention, a compound, stereoisomer, or pharmaceutically acceptable salt or ester thereof is provided that conforms to Formula (IIa):

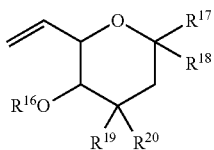
(IIa)

where
$R^{16}$ is H or an optionally substituted polyethylene glycol moiety;
$R^{17}$ and $R^{18}$ are independently selected from the group consisting of H, $C_{1-6}$-alkyl, and $C_{1-6}$-alkyl substituted with one to three groups independently selected from halo, hydroxy, and $C_{1-6}$-alkoxy; and
$R^{19}$ and $R^{20}$ are independently selected from the group consisting of hydrogen, halo($C_{1-6}$-alkyl), C(O)$R^{21}$, F, Cl, $NO_2$, and B(O$R^{21}$)$_2$, wherein at least one of $R^{19}$ and $R^{20}$ is other than hydrogen, and wherein each $R^{21}$ is independently H, $C_{1-6}$-alkyl, or halo($C_{1-6}$-alkyl),
or $R^{19}$ and $R^{20}$, together with the carbon atom to which they are both bound, form an epoxide ring or carbonyl group.

In one embodiment, provided is a compound having Formula (IIb):

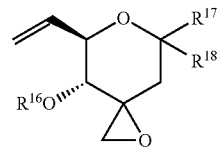
(IIb)

wherein $R^{16}$, $R^{17}$, and $R^{18}$ are as previously defined in Formula (IIa).

In some embodiments, at least one of $R^{17}$ and $R^{18}$ is selected from the group consisting of $C_{1-6}$-alkyl and $C_{1-6}$-alkyl substituted with one to three groups independently selected from halo, hydroxy, and $C_{1-6}$-alkoxy. In other embodiments, at least one of $R^{17}$ and $R^{18}$ is independently selected from the group consisting of $CH_3$, $CH_2I$, and $CH_2OH$. In still other embodiments, each of $R^{17}$ and $R^{18}$ is methyl.

In some embodiments, $R^{19}$ and $R^{20}$, together with the carbon atom to which they are both bound, form a carbonyl group.

In some embodiments $R^{16}$, $R^{19}$, and $R^{20}$ together with the carbon atoms to which they are bound, represent the following structure:

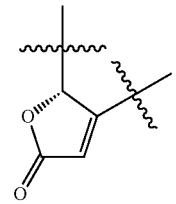

In some embodiments, $R^{17}$ and $R^{18}$ is methyl, and $R^{19}$ and $R^{20}$, together with the carbon atom to which they are both bound, form a carbonyl group.

Exemplary compounds of the present invention include:

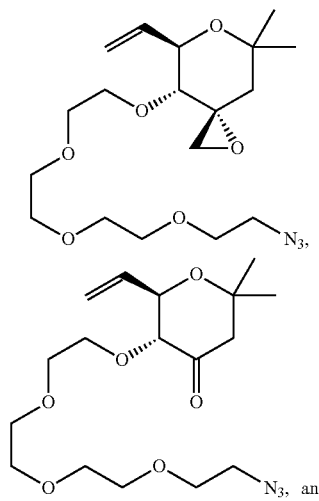

-continued

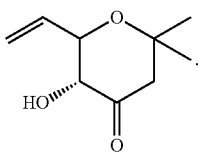

The general embodiments described above are illustrated by the following exemplary compounds:

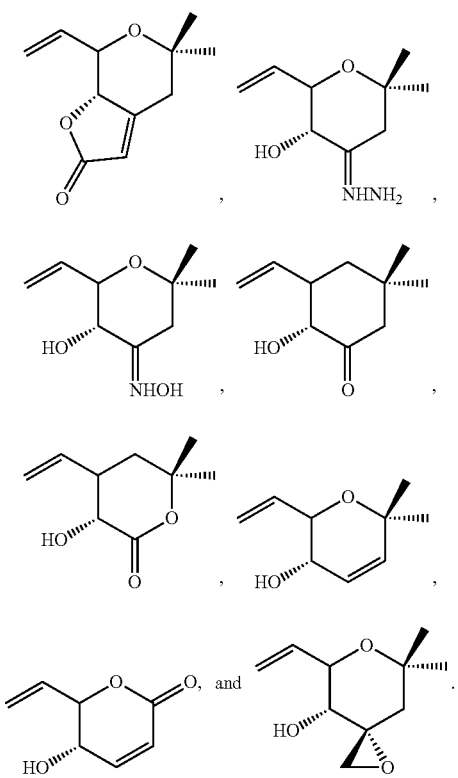

Methods and Uses

Other embodiments are methods and uses for treating a cellular proliferative disorder in a subject, comprising administering to the subject a therapeutically effective amount of any of the embodiments of a compound, stereoisomer, or pharmaceutically acceptable salt or ester thereof of Formula (Ia), (Ib), (Ic), (Id), (IIa), or (IIb).

Not wishing to be bound by any particular theory, the inventors believe that the compounds described herein inhibit RNA splicing. The invention therefore contemplates in other embodiments a method of treating a disease or disorder that is associated with RNA splicing. Illustrative of this category of RNA splicing-related conditions are cystic fibrosis, Duchenne muscular dystrophy, Fanconi anemia, and neurofibromatosis, among other genetic diseases, as well as a cellular proliferative disorder described above, e.g., breast cancer, ovarian cancer, colon cancer, lung cancer, kidney cancer, oral cancer and prostate cancer. Dysfunctional RNA splicing is understood also to play a role in various inflammatory diseases, such as rheumatoid arthritis and psoriasis, in certain cardiovascular disorders, and in the pathology of infections by oncogenic viruses and other virus types, such as Borna disease virus and HIV, by parasitic infections and fungal infections.

Administration and Pharmaceutical Composition

In general, the compounds of this invention are administered in a therapeutically effective amount by any of the accepted modes of administration for agents that serve similar utilities. The actual amount of the compound of this invention, as the active ingredient, will depend upon numerous factors, such as the severity of the disease to be treated, the age and relative health of the subject, the potency of the compound used, the route and form of administration, and other factors. The drug can be administered more than once a day, such as once or twice a day. Assessing each of these factors is within the skill of the attending clinician.

Therapeutically effective amounts of the compounds can range from approximately 0.05 to 50 mg per kilogram body weight of the recipient per day; such as about 0.1-25 mg/kg/day, or from about 0.5 to 10 mg/kg/day. Thus, for administration to a 70 kg person, for instance, the dosage range can be about 35-70 mg per day.

The compounds can be used alone or in compositions together with a pharmaceutically acceptable carrier or excipient. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Exemplary liquid carriers, particularly for injectable solutions, include water, saline, aqueous dextrose, and glycols. Other suitable, pharmaceutically acceptable excipients are described in REMINGTON'S PHARMACEUTICAL SCIENCES, Mack Pub. Co., New Jersey (1991), incorporated herein by reference.

In general, compounds of the invention are administered as pharmaceutical compositions by any one of the following routes: oral, systemic (e.g., transdermal, intranasal or by suppository), parenteral (e.g., intramuscular, intravenous or subcutaneous), or intrathecal administration. One manner of administration is oral, using a convenient daily dosage regimen that is adjusted according to the degree of affliction. Compositions can take the form of tablets, pills, capsules, semisolids, powders, sustained release formulations, solutions, suspensions, elixirs, aerosols, ointments, or any other appropriate compositions. Another manner for administering an inventive compounds is inhalation, which delivers a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. Inert gases suitable for this purpose are nitrogen, carbon dioxide, etc. There are several types of pharmaceutical inhalation devices-nebulizer inhalers, metered dose inhalers (MDI), and dry powder inhalers (DPI). Nebulizer devices produce a stream of high velocity air that causes the therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The amount of the compound in a formulation can vary within the full range employed by those skilled in the art. Typically, the formulation contains, on a weight percent (wt %) basis, from about 0.01-99.99 wt % of the compound of based on the total formulation, with the balance being one or more suitable pharmaceutical excipients. For example, in some embodiments the compound is present at a level of about 1-80 wt %.

In some embodiments provided is a pharmaceutical composition comprising a compound, stereoisomer, or pharmaceutically acceptable salt or ester thereof of Formula (I), (Ia), (Ib), (Ic), or (Id) and a pharmaceutically acceptable carrier.

In some embodiments, the composition comprises a compound or pharmaceutically acceptable salt or ester thereof having one of the following formulas:

Other embodiments provide a pharmaceutical composition comprising a compound of Formula (II), (IIa) or (IIb), stereoisomer, or pharmaceutically acceptable salt or ester thereof and a pharmaceutically acceptable carrier.

In some embodiments, the composition comprises a compound or pharmaceutically acceptable salt or ester thereof with at least one of the following formulae:

General Synthetic Methods

Compounds of this invention are prepared from readily available starting materials using the following general methods and procedures. It will be appreciated that where typical process conditions (i.e., reaction temperatures, times, mole ratios of reactants, solvents, pressures, etc) are given, other process conditions can also be used unless otherwise stated. Optimum reaction conditions vary with the particular reactants or solvent used, but such conditions are determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Greene and Wuts, supra.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers and enriched mixtures are included within the scope of this invention, unless otherwise indicated. Pure stereoisomers (or enriched mixtures) are prepared using, for example, optically active starting materials or stereoselective reagents well-known in the art. Alternatively, racemic mixtures of such compounds are separated using, for example, chiral column chromatography, chiral resolving agents and the like.

The various starting materials, intermediates, and compounds of the invention are isolated and purified where appropriate using conventional techniques such as precipitation, filtration, crystallization, evaporation, distillation, and chromatography. Characterization of these compounds are performed using conventional methods such as by melting point, mass spectrum, nuclear magnetic resonance, and various other spectroscopic analyses.

In one embodiment, provided is a process for preparing a compound, stereoisomer, or pharmaceutically acceptable salt or ester thereof having Formula (Ia):

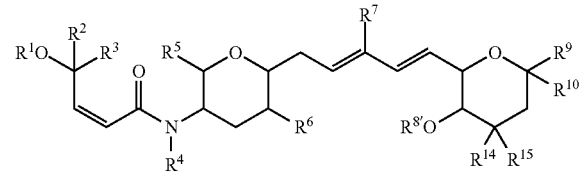

(Ia)

wherein
$R^1$ is selected from the group consisting of H, Pg, $C_{1-6}$-alkyl, halo($C_{1-6}$-alkyl), C(O)$R^{11}$, C(O)O$R^{11}$, and C(O)N$R^{12}R^{13}$,
  wherein each $R^{11}$ is independently H, $C_{1-6}$-alkyl, or halo($C_{1-6}$-alkyl), and
  wherein $R^{12}$ and $R^{13}$ are independently selected from the group consisting of H, $C_{1-6}$-alkyl, and halo($C_{1-6}$-alkyl); or $R^{12}$ and $R^{13}$, together with the nitrogen atom to which they are bound, form a heterocyclic or heteroaromatic ring;
$R^2$, $R^3$, $R^4$, $R^5$, and $R^6$ are independently selected from the group consisting of H, $C_{1-6}$-alkyl, and halo($C_{1-6}$-alkyl);
$R^7$ is selected from the group consisting of H, $C_{1-6}$-alkyl and halo($C_{1-6}$-alkyl);
$R^{8'}$ is an optionally substituted polyethylene glycol; and
$R^9$ and $R^{10}$ are independently selected from the group consisting of H, $C_{1-6}$-alkyl, and $C_{1-6}$-alkyl substituted with one to three groups independently selected from halo, hydroxy, $C_{1-6}$-alkoxy, and OPg;

$R^{14}$ or $R^{15}$ are selected independently from the group consisting of halo($C_{1-6}$-alkyl), C(O)$R^{11}$, F, Cl, NO$_2$, and B(O$R^{11}$)$_2$, wherein $R^{11}$ is as defined above, and at least one of $R^{14}$ and $R^{15}$ is other than hydrogen; and
each Pg is independently a hydroxy protecting group;
said method comprising the steps of:
(A) contacting a compound of Formula (III):

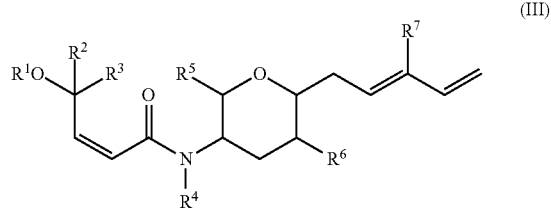

(III)

wherein $R^1$, $R^2$, $R^3$, $R^4$, $R^5$, $R^6$, and $R^7$ are as defined above with a compound of Formula (IIa):

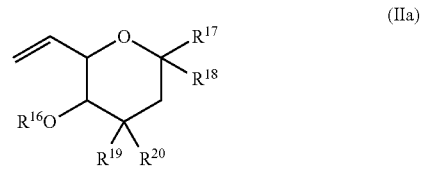

(IIa)

wherein $R^{16}$ is hydrogen and $R^{17}$, $R^{18}$, $R^{19}$, and $R^{20}$ are as defined above, in the presence of an olefin metathesis catalyst;
and if $R^{8'}$ is an optionally substituted polyethylene glycol, then the method further comprises
(B) contacting the product of step (A) with a compound of the formula (IV)

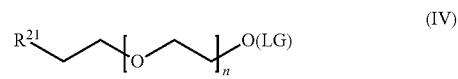

(IV)

wherein
$R^{21}$ is selected from the group consisting of azide, tetrazole and triazole with hydrogen, alkyl, or substituted alkyl substituents;
n is an integer selected from 1, 2, 3, 4, 5, and 6; and
LG is a leaving group.

In accordance with one aspect of the invention, the compound of Formula (Ia) made by the above process is:

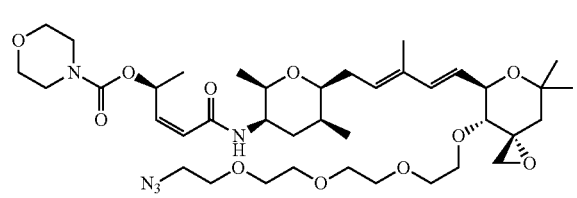

In accordance with one aspect of the invention, the compound of Formula IIa, used in the process of making the compound of Formula (Ia), is prepared by contacting a compound of Formula (V):

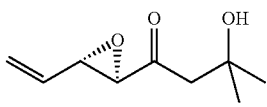

(V)

with an acidic reagent. In some embodiments, the acidic reagent is camphorsulfonic acid. In other embodiments, the acidic reagent is a silica gel.

According to one aspect of the invention, the compound of Formula (IIa), used in the process of making the compound of formula (Ia), is the following compound:

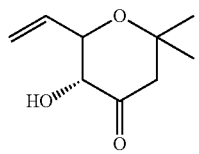

The following examples illustrate certain embodiments of the present invention to aid the skilled person in practicing the invention. Accordingly, the examples are in no way considered to limit the scope of the invention.

EXAMPLES

General techniques. All reactions were carried out with freshly distilled solvents under anhydrous conditions, unless otherwise noted. Tetrahydrofuran (THF) was distilled over Na metal and benzophenone. Methylene chloride (CH$_2$Cl$_2$) was distilled over calcium hydride. Acetonitrile was distilled from CaH$_2$ and stored over 3 Å molecular sieves. Yields refer to chromatographically and spectroscopically ($^1$H NMR) homogenous materials, unless otherwise stated.

All reactions were monitored by thin-layer chromatography (TLC) carried out on 0.25 mm Merck silica gel plates (60E-254) using UV light (254 nm) for visualization or anisaldehyde in ethanol or 0.2% ninhydrin in ethanol as a developing agents and heat for visualization. Silica gel (230-400 mesh) was used for flash column chromatography. A rotary evaporator was connected to a water aspirator that produced a vacuum pressure of approximately 60 mmHg when it was connected to the evaporator.

NMR spectra were recorded on a Bruker Advance spectrometer at 300 MHz, 400 MHz, 500 MHz, 600 MHz or 700 MHz. The chemical shifts are given in parts per million (ppm) on a delta ($\delta$) scale. The solvent peak was used as a reference value, for $^1$H NMR: CHCl$_3$=7.27 ppm, MeOH=3.31 ppm, DMSO=2.50 ppm, acetone=2.05 ppm, for $^{13}$C NMR: CDCl$_3$=77.00 ppm, CD$_3$OD=49.00 ppm, DMSO-d$_6$=49.10 ppm and acetone-d$_6$=29.40 ppm. The following abbreviations are used to indicate the multiplicities: s=singlet; d=doublet; t=triplet; q=quartet; m=multiplet; br=broad.

High-resolution mass spectra were recorded on a VG 7070 spectrometer. Low-resolution mass spectra [LCMS (ESI)] were recorded on a Shimadzu LCMS-2020. Infrared (IR) spectra were collected on a Mattson Cygnus 100 spectrometer. Samples for acquiring IR spectra were prepared as a thin film on a NaCl plate by dissolving the compound in CH$_2$Cl$_2$ and then evaporating the CH$_2$Cl$_2$.

Abbreviations: Ac, acetyl; br, broad; Cp, cyclopentadienyl; CSA, Camphorsulfonic Acid; DIBALH, Diisobutylaluminum hydride; EI, electron impact; ES, electrospray; Et, ethyl; EtOAc, ethyl acetate; EtOH, ethanol; HRMS, high resolution mass spectrum; Me, methyl; MeOH, methanol; Ph, phenyl; RT-PCR, Reverse transcriptase-polymerase chain reaction; Tf, trifluoromethanesulfonyl; THF, tetrahydrofuran; TMSCL, Trimethylsilyl chloride.

Example 1

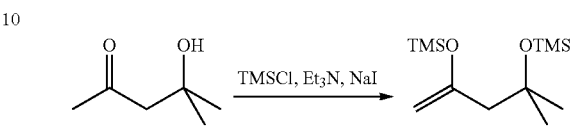

Preparation of 2,2,4,4,8,8-hexamethyl-6-methylene-3,7-dioxa-2,8-disilanonane: A 1-L round-bottomed flask equipped with a Teflon-coated magnetic stir bar containing 4-hydroxy-4-methyl-2-pentanone (22 g, 189 mmol) was purged with argon. Et$_3$N (66 mL, 435 mmol) and TMSCl (55 mL, 491 mmol) were added to the flask at 23° C. and the mixture was stirred at the same temperature for 30 min. A solution of NaI (75 g, 500 mmol) in MeCN (850 mL) was added to the reaction mixture over 1 h at the same temperature. The mixture was stirred for an additional 3.5 h, then diluted with ice cold H$_2$O (1.5 L). The mixture was extracted with EtOAc (5×500 mL). The combined organic layers were dried over Na$_2$SO$_4$, filtered, and concentrated in vacuo. The resulting crude residue of 2,2,4,4,8,8-hexamethyl-6-methylene-3,7-dioxa-2,8-disilanonane (34 g, 70% yield) was <90% pure by $^1$H NMR, and used directly in the next step without further purification.

Data for 2,2,4,4,8,8-hexamethyl-6-methylene-3,7-dioxa-2,8-disilanonane: IR (film): $\nu_{max}$=2961, 1620, 1321, 1251, 1042 cm$^{-1}$; $^1$H NMR (300 MHz, CDCl$_3$, 293 K): $\delta$=4.08 (d, J=3.3 Hz, 2H, 1'-, 1-H), 2.21 (s, 2H, 2-H), 1.28 (s, 6H, 3-H), 0.23 (s, 9H, TMS), 0.12 (s, 9H, TMS); $^{13}$C NMR (100 MHz, CDCl$_3$, 293 K): $\delta$=157.0, 92.7, 73.8, 51.8, 29.9, 2.7, 0.04; HRMS of compound 2,2,4,4,8,8-hexamethyl-6-methylene-3,7-dioxa-2,8-disilanonane was not obtainable.

Example 2

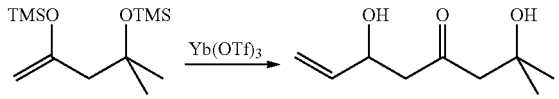

Preparation of 2,6-dihydroxy-2-methyloct-7-en-4-one: To a 1-L round-bottomed flask equipped with a Teflon-coated magnetic stir bar containing 2,2,4,4,8,8-hexamethyl-6-methylene-3,7-dioxa-2,8-disilanonane (1.9 g, 7.3 mmol), was added toluene (15 mL) and acrolein (11.6 mL, 174 mmol). The flask was cooled on an ice-water bath (0° C. external temperature), then a solution of Yb(OTf)$_3$ (533 mg, 0.86 mmol) in H$_2$O:EtOH (1:10, 4.1 mL) was added. The mixture was stirred at the same temperature for 24 h, then diluted with brine (30 mL). The organic solvents were removed in vacuo, then the resulting mixture was extracted with EtOAc (3×20 mL). The combined organic layers were dried over Na$_2$SO$_4$, filtered and concentrated in vacuo. The crude residue was purified by flash chromatography (10→80% EtOAc in hexanes) on silica gel (100 mL) to afford 2,6-dihydroxy-2-methyloct-7-en-4-one as a clear oil (903 mg, 72% yield).

Data for 2,6-dihydroxy-2-methyloct-7-en-4-one: $R_f$=0.18 (40% EtOAc in hexanes); IR (film): $v_{max}$=3410 (br O—H), 2974, 2932, 1701 (C=O), 1378, 1144 cm$^{-1}$; $^1$H NMR (300 MHz, 1% CD$_3$OD in CDCl$_3$, 293 K): δ=5.87 (ddd, J=5.6, 10.4, 16.8 Hz, 1H, 2-H), 5.31 (ddd, J=16.8, 1.2, 1.2 Hz, 1H, 1$_{trans}$-H), 5.16 (ddd, J=10.4, 1.2, 1.2 Hz, 1H, 1$_{cis}$-H), 4.61 (ddddd, J=8.8, 6.0, 6.0, 1.2, 1.2 Hz, 1H, 3-H), 2.73-2.63 (m, 4H, 2-H, 5-H), 1.25 (s, 6H, 6-H); $^{13}$C NMR (100 MHz, CDCl$_3$, 293 K): δ=212.5, 138.8, 115.3, 69.8, 68.6, 54.2, 50.5, 29.4; HRMS (ESI+) calcd. for C$_9$H$_{17}$O$_3$ [M+H]$^+$ 173.1178. found 173.1184.

Example 3

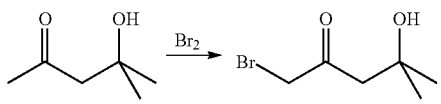

Preparation of 1-bromo-4-hydroxy-4-methylpentan-2-one: To a 250-mL round-bottomed flask equipped with a Teflon-coated magnetic stir bar was added 4-hydroxy-4-methylpentan-2-one (10 g, 86.1 mmol), MeOH (60 mL) and the stirred solution was cooled to 0° C. To the mixture was added Br$_2$ (4.4 mL, 86.1 mmol) dropwise and the resultant mixture was stirred at 0° C. for 2 h. The mixture was poured into 200 mL water and extracted the aqueous layer with CH$_2$Cl$_2$ (50 mL×4 times). The organic layer was separated, dried over Na$_2$SO$_4$, filtered, and concentrated in vacuo to afford 1-bromo-4-hydroxy-4-methylpentan-2-one as a clear oil (16.6 g, 99% yield).

Data for 1-bromo-4-hydroxy-4-methylpentan-2-one: $R_f$=0.57 (60% EtOAc in hexanes); IR (film): $v_{max}$=3433 (br O-H), 2975, 2249, 1715 (C=O), 1465, 1382, 1173, 1057, 978, 911, 733 cm$^{-1}$; $^1$H NMR (300 MHz, 1% CD$_3$OD in CDCl$_3$, 293 K): δ=3.89 (s, 2H), 2.72 (s, 2H), 1.18 (s, 6H); $^{13}$C NMR (125 MHz, CDCl$_3$, 293 K): δ=202.8, 70.0, 51.0, 35.6, 29.4; HRMS (EI+) calcd. for C$_6$H$_{12}$BrO [M-OH+H]$^+$ 179.0066. found 178.9959.

Example 4

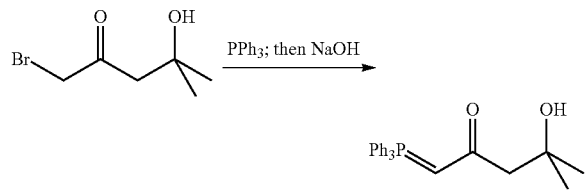

Preparation of 4-hydroxy-4-methylpentan-2-one phosphonium ylide: To a 250-mL round-bottomed flask equipped with a Teflon-coated magnetic stir bar was added 1-bromo-4-hydroxy-4-methylpentan-2-one (10 g, 51.2 mmol), benzene (80 mL), PPh$_3$ (14 g, 53 mmol) and the solution was stirred at 23° C. for 7 h. The mixture was poured into 1 L water and extracted the aqueous layer with CH$_2$Cl$_2$ (100 mL×3 times). To the aqueous layer was added 4 M NaOH (15 mL, 60 mmol) and extracted the white aqueous suspension with CH$_2$Cl$_2$ (100 mL×4). The organic layer was separated, dried over Na$_2$SO$_4$, filtered and concentrated in vacuo to afford crude ylide 4-hydroxy-4-methylpentan-2-one phosphonium ylide which was washed with hexanes (100 mL×3) until TLC analysis showed absence of PPh$_3$ in the yellowish white solid ylide 4-hydroxy-4-methylpentan-2-one phosphonium ylide (12.3 g, 64% yield).

Data for 4-hydroxy-4-methylpentan-2-one phosphonium ylide: $R_f$=0.0-0.24 streak (40% EtOAc in hexanes); IR (film): $v_{max}$=3266 (br O—H), 3057, 2967, 1675 (C=O), 1528, 1437, 1404, 1282, 1106, 998 cm$^{-1}$; $^1$H NMR (300 MHz, 1% CD$_3$OD in CDCl$_3$, 293 K): δ=7.65-7.43 (m, 15H), 3.80-3.71 (d, J=26.1 Hz, 1H), 2.43 (s, 2H), 1.24 (s, 6H); $^{13}$C NMR (125 MHz, CDCl$_3$, 293 K): δ=192.9, 133.1 (d, J=10 Hz), 132.2 (d, J=2.5 Hz), 129.0 (d, J=11.3 Hz), 126.3 (d, J=90 Hz), 70.1, 55.7 (d, J=103.8 Hz), 50.3 (d, 13.8), 29.7; HRMS (EI+) calcd. for C$_{24}$H$_{26}$O$_2$P [M+H]$^+$ 377.1665. found 377.1675. m.p.: 185° C.

Example 5-a

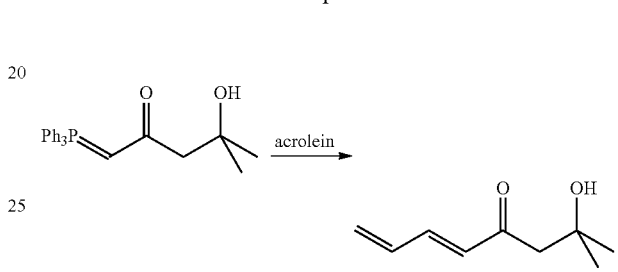

Preparation of (E)-2-hydroxy-2-methylocta-5,7-dien-4-one (Method A): To a 100-mL round-bottomed flask equipped with a Teflon-coated magnetic stir bar was added 4-hydroxy-4-methylpentan-2-one phosphonium ylide (572 mg, 1.5 mmol), CH$_2$Cl$_2$ (5 mL), at 23° C. and to it was added acrolein (103 mg, 1.8 mmol) dropwise. The mixture was stirred at the same temperature for 24 h. The mixture was concentrated in vacuo. The crude residue was purified by flash chromatography (10→50% EtOAc in hexanes) on silica gel (30 mL) to afford (E)-2-hydroxy-2-methylocta-5,7-dien-4-one as a clear oil (67 mg, 29% yield).

Example 5-b

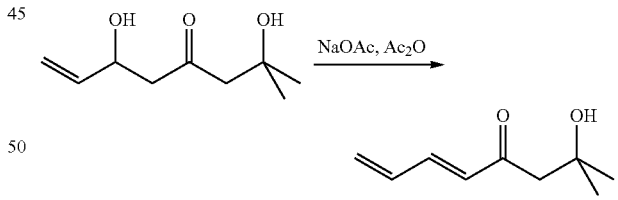

Preparation of (E)-2-hydroxy-2-methylocta-5,7-dien-4-one (Method B): To a 250-mL round-bottomed flask equipped with a Teflon-coated magnetic stir bar was added 2,6-dihydroxy-2-methyloct-7-en-4-one (10.7 g, 62.2 mmol), DCE (40 mL), Ac$_2$O (6.20 mL, 62.2 mmol) and NaOAc (1.50 g, 18.7 mmol). The mixture was stirred in a 60° C. oil bath for 24 h. The mixture was cooled to 23° C., then diluted with EtOAc (150 mL) and saturated aqueous sodium bicarbonate (200 mL). The organic layer was separated, dried over Na$_2$SO$_4$, filtered, and concentrated in vacuo. The crude residue was purified by flash chromatography (10→50% EtOAc in hexanes) on silica gel (100 mL) to afford (E)-2-hydroxy-2-methylocta-5,7-dien-4-one as a clear oil (6.7 g, 70% yield).

Example 5-c

Preparation of (E)-2-hydroxy-2-methylocta-5,7-dien-4-one (Method C): To a 25-mL round-bottomed flask equipped with a Teflon-coated magnetic stir bar was added (5R,6R)-5-hydroxy-2,2-dimethyl-6-vinyldihydro-2H-pyran-4(3H)-one (110 mg, 0.6 mmol), DCE (1 mL), Piv$_2$O (0.14 mL, 0.7 mmol) and NaOAc (25 mg, 0.3 mmol). The mixture was stirred in a 60° C. oil bath for 24 h. The mixture was cooled to 23° C., then diluted with CH$_2$Cl$_2$ (5 mL) and saturated aqueous sodium bicarbonate (5 mL). The organic layer was separated, dried over Na$_2$SO$_4$, filtered, and concentrated in vacuo. The crude residue was purified by flash chromatography (10→50% EtOAc in hexanes) on silica gel (10 mL) to afford (E)-2-hydroxy-2-methylocta-5,7-dien-4-one as a clear oil (77 mg, 83% yield).

Data for (E)-2-hydroxy-2-methylocta-5,7-dien-4-one: R$_f$=0.33 (40% EtOAc in hexanes); IR (film): ν$_{max}$=3437 (br 0-H), 2973, 1678 (C=O), 1204, 1110 cm$^{-1}$; $^1$H NMR (300 MHz, 1% CD$_3$OD in CDCl$_3$, 293 K): δ=7.16 (dd, J=15.6 Hz, 10.8 Hz, 1H, 3-H), 6.48 (ddd, J=16.8, 10.8, 10.8 Hz, 1H, 2-H), 6.18 (d, J=15.6 Hz, 1H, 4-H), 5.72 (d, J=16.8 Hz, 1H, 1$_{trans-H}$), 5.60 (d, J=10.8 Hz, 1H, 1$_{cis}$-H), 2.77 (s, 2H, 5-H), 1.29 (s, 6H, 6-H); $^{13}$C NMR (75 MHz, CDCl$_3$, 293 K): δ=202.0, 143.6, 135.0, 131.0, 127.4, 69.9, 50.5, 29.4; HRMS (EI+) calcd. for C$_9$H$_{14}$O$_2$ [M-CH$_3$]$^+$ 139.0759. found 139.0756.

Example 6

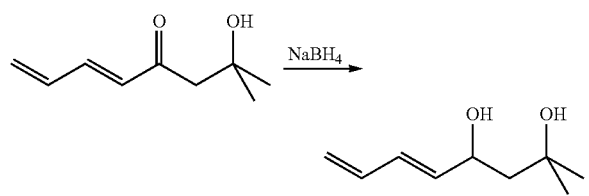

Preparation of (E)-2-methylocta-5,7-diene-2,4-diol: A 500-mL round-bottomed flask equipped with a Teflon-coated magnetic stir bar was added (E)-2-hydroxy-2-methylocta-5,7-dien-4-one (2.4 g, 15.4 mmol) and MeOH (60 mL). The mixture was cooled to 0° C. and NaBH$_4$ (1.16 g, 30.8 mmol) was added over 15 min. The mixture was stirred at the same temperature for 30 min, then diluted with saturated aqueous NH$_4$Cl (50 mL). MeOH was removed in vacuo, then the resulting mixture was extracted with EtOAc (3×20 mL). The combined organic layers were dried over Na$_2$SO$_4$, filtered, and concentrated in vacuo. The crude (E)-2-methylocta-5,7-diene-2,4-diol was used directly in the next step.

Data for (E)-2-methylocta-5,7-diene-2,4-diol: R$_f$=0.30 (40% EtOAc in hexanes); IR (film): ν$_{max}$=3369, 3088, 3040, 2973, 2935, 1654, 1605, 1467, 1380, 1326, 1253, 1153, 1058, 1004, 952, 908, 857, 768 cm$^{-1}$; $^1$H NMR (300 MHz, 1% CD$_3$OD in CDCl$_3$, 293 K): δ=6.05-6.25 (ddd, J=16.2, 10.2, 10.2 Hz, 1H), 6.05-6.25 (dd, J=14.4, 10.5 Hz, 1H), 5.53 (dd, J=14.7, 6.3 Hz, 1H), 5.05 (d, J=14.4 Hz, 1H), 4.93 (d, J=9.9 Hz, 1H), 4.40 (dd, J=7.8, 6.3 Hz, 1H), 1.60 (dd, J=14.4, 10.8, 1H), 1.43 (dd, J=14.4, 2.4, 1H), 1.20 (s, 3H), 1.11 (s, 3H); $^{13}$C NMR (75 MHz, CDCl$_3$, 293 K): δ=136.4, 130.2, 130.0, 117.1, 71.3, 69.8, 47.5, 31.4, 27.6.

Example 7

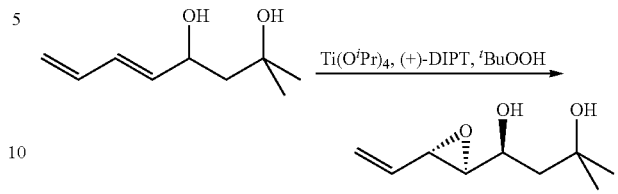

Preparation of (S)-3-methyl-1-((2S,3S)-3-vinyloxiran-2-yl)butane-1,3-diol: A 250-mL round-bottomed flask equipped with a Teflon-coated magnetic stir bar containing the crude (E)-2-methylocta-5,7-diene-2,4-diol was purged with argon. CH$_2$Cl$_2$ (60 mL) and 4 Å M.S. (3.1 g) were added to the flask. The mixture was cooled to −20° C. (external temperature), then Ti(O$^i$Pr)$_4$ (0.38 g, 1.34 mmol), (+)-DIPT (0.5 g, 2.1 mmol) and tBuOOH solution in isooctane (1.4 mL, 8.0 mmol) were added sequentially at the same temperature. The mixture was stirred at the same temperature for 13 h, then diluted with 1 M NaOH (50 mL), Celite® (3.0 g), Na$_2$SO$_4$ (3.0 g), NaCl (3.0 g). The mixture was stirred for 40 min, then filtered through a pad of Celite® and florisil mixture. The filtrate was concentrated in vacuo, and the resulting crude residue was purified by flash chromatography (10→70% EtOAc in hexanes) on silica gel (200 mL) to afford the (S)-3-methyl-1-((2S,3S)-3-vinyloxiran-2-yl)butane-1,3-diol as a clear oil (0.8 g) with impurities of titanium and tartarate. The impure epoxide (S)-3-methyl-1-((2S,3S)-3-vinyloxiran-2-yl)butane-1,3-diol was used in the next step without further purification.

Data for (S)-3-methyl-1-((2S,3S)-3-vinyloxiran-2-yl)butane-1,3-diol: R$_f$=0.35 (60% EtOAc in hexanes); IR (film): ν$_{max}$=3400, 2977, 2932, 1645, 1425, 1371, 1255, 1147, 1064, 1022, 929, 905, 796, 737. cm$^{-1}$; $^1$H NMR (300 MHz, 1% CD$_3$OD in CDCl$_3$, 293 K): δ=5.89-5.78 (ddd, J=17.4, 10.5, 6.9 Hz, 1H), 5.31 (d, J=17.4 Hz, 1H), 5.23 (d, J=10.5 Hz, 1H), 3.7 (m, 2H), 3.08 (dd, J=9.0, 9.3 Hz, 1H), 1.89 (dd, J=12.9, 5.1 Hz, 1H), 1.24 (m, 7H); $^{13}$C NMR (75 MHz, CDCl$_3$, 293 K): δ=136.3, 118.5, 76.4, 75.1, 73.1, 70.3, 70.1, 43.5, 31.2, 23.0.

Example 8

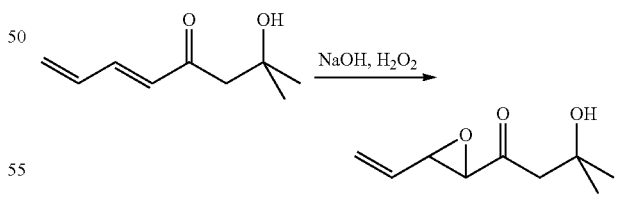

Preparation of 3-hydroxy-3-methyl-1-(3-vinyloxiran-2-yl)butan-1-one: A 50-mL round-bottomed flask equipped with a Teflon-coated magnetic stir bar containing (E)-2-methylocta-5,7-diene-2,4-diol (390 mg, 2.50 mmol) was charged with MeOH (13 mL). The flask was cooled on an ice-water bath (0° C. external temperature). H$_2$O$_2$ (1 mL, 12.5 mmol) and aqueous 1M NaOH (0.46 mL, 0.5 mmol) were added to the reaction mixture at the same temperature. The mixture was stirred at the same temperature for 3.5 h, then diluted with saturated aqueous NH$_4$Cl (10 mL). The mixture was extracted with Et$_2$O (3×10 mL). The combined organic layers were dried over Na$_2$SO$_4$, filtered, and concentrated in vacuo. The crude residue was purified by flash chromatography (5→30% EtOAc in hexanes) on silica gel (25 mL) to afford 3-hydroxy-3-methyl-1-(3-vinyloxiran-2-yl)butan-1-one as a clear oil (309 mg, 73% yield).

Data for epoxide 3-hydroxy-3-methyl-1-(3-vinyloxiran-2-yl)butan-1-one: R$_f$=0.33 (40% EtOAc in hexanes); IR (film): ν$_{max}$=3403 (br, O—H), 2974, 2930, 1709 (C=O), 1442, 1199, 1135 cm$^{-1}$; $^1$H NMR (300 MHz, CDCl$_3$, 293 K): δ=5.56 (ddd, J=17, 11, 6 Hz, 1H, 2-H), 5.55 (dd, J=17, 2.5 Hz, 1H, 1$_{trans-H}$), 5.41 (dd, J=11, 2.5 Hz, 1H, 1$_{cis}$-H), 3.49 (dd, J=6, 2.1 Hz, 1H, 3-H), 3.38 (d, J=2.1 Hz, 1H, 4-H), 2.67 (d, J=17.1 Hz, 1H, 5-H), 2.50 (d, J=17.1 Hz, 1H, 5-H), 1.28 (s, 3H, 6-H), 1.27 (s, 3H, 6-H); $^{13}$C NMR (175 MHz, CDCl$_3$, 293 K): δ=207.9, 133.0, 121.8, 69.8, 61.2, 57.9, 47.9, 29.5, 29.4; HRMS (EI+) calcd. for C$_9$H$_{13}$O$_2$ [M-OH]$^+$ 153.0916. found 153.0910.

Example 9

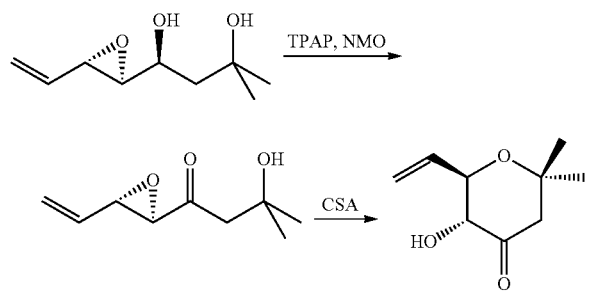

Preparation of (5R,6R)-5-hydroxy-2,2-dimethyl-6-vinyldihydro-2H-pyran-4(3H)-one: To a 1-L round-bottomed flask equipped with a Teflon-coated magnetic stir bar containing the (S)-3-methyl-1-((2S,3S)-3-vinyloxiran-2-yl)butane-1,3-diol (0.8 g) was added CH$_2$Cl$_2$ (200 mL), 4 Å M.S. (3.3 g), TPAP (101 mg, 0.29 mmol) and NMO (2.5 g, 18.4 mmol) at 23° C. The mixture was stirred at the same temperature for 40 min, then filtered through a plug of silica. The filtrate was concentrated to approximately 200 mL of CH$_2$Cl$_2$ remained in the flask. To the flask was added CSA (860 mg, 3.7 mmol) at 23° C. The mixture was stirred at the same temperature for 19 h, then Et$_3$N (1 mL) was added. The mixture was concentrated in vacuo, and the crude residue was purified by flash chromatography (10→30% EtOAc in hexanes) on silica gel (50 mL) to afford (5R,6R)-5-hydroxy-2,2-dimethyl-6-vinyldihydro-2H-pyran-4(3H)-one as a clear oil (512 mg, 20% yield, over 4 steps).

Data for (5R,6R)-5-hydroxy-2,2-dimethyl-6-vinyldihydro-2H-pyran-4(3H)-one: R$_f$=0.35 (30% EtOAc in hexanes); IR (film): ν$_{max}$=3474 (br, O—H), 2975, 2934, 1723 (C=O), 1374, 1240, 1107, 1080 cm$^{-1}$; $^1$H NMR (300 MHz, 1% CD$_3$OD in C$_6$D$_6$, 293 K): δ=6.16 (ddd, J=17.1, 10.5, 4.8 Hz, 1H, 2-H), 5.53 (ddd, J=17.1, 1.8, 1.8 Hz, 1H, 1$_{trans-H}$), 5.17 (ddd, J=10.5, 1.8, 1.8 Hz, 1H, 1$_{cis}$-H), 3.86 (dd, J=9.0, 6.8 Hz, 1H, 3-H), 3.63 (d, J=9.0 Hz, 1H, 4-H), 1.00 (s, 3H, 6-H), 0.75 (s, 3H, 6-H); $^{13}$C NMR (75 MHz, CDCl$_3$, 293 K): δ=207.4, 135.5, 118.0, 77.9, 76.7, 76.4, 51.5, 30.8, 23.6; HRMS (ESI+) calcd. for C$_9$H$_{15}$O$_3$ [M+H]$^+$ 171.1021. found 171.1006. [α]$_D^{20}$ +28.1 (c 1.0, CH$_2$Cl$_2$).

Example 10

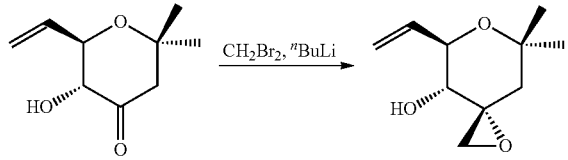

Preparation of (3R,4R,5R)-7,7-dimethyl-5-vinyl-1,6-dioxaspiro[2.5]octan-4-ol: A 25-mL round-bottomed flask equipped with a Teflon-coated magnetic stir bar containing (5R,6R)-5-hydroxy-2,2-dimethyl-6-vinyldihydro-2H-pyran-4(3H)-one (200 mg, 1.18 mmol) was purged with N$_2$. To the flask was added THF (12 mL) and CH$_2$Br$_2$ (246 mg, 1.42 mmol). The flask was cooled to −78° C., then $^n$BuLi (1.6 mL, 2.6 mmol) was added. The mixture was stirred for 7 h, while warming the cooling bath to 20° C. The reaction mixture was quenched with saturated aqueous NH$_4$Cl (15 mL), and THF was removed in vacuo. The resulting mixture was extracted with Et$_2$O (3×15 mL). The combined organic layers were dried over Na$_2$SO$_4$, filtered and concentrated in vacuo. The crude residue was purified by flash chromatography (5→30% EtOAc in hexanes) on silica gel (40 mL) to afford (3R,4R,5R)-7,7-dimethyl-5-vinyl-1,6-dioxaspiro[2.5]octan-4-ol as a clear oil (157 mg, 73% yield).

Spectroscopic data for (3R,4R,5R)-7,7-dimethyl-5-vinyl-1,6-dioxaspiro[2.5]octan-4-ol matches those in *J. Am. Chem. Soc.* 2007, 129, 2648-2659.

Example 11

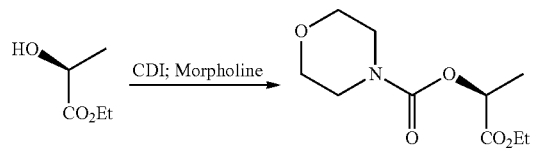

Preparation of (S)-1-ethoxy-1-oxopropan-2-yl morpholine-4-carboxylate: Synthesis and spectroscopic characterization are well known in the art. For example, refer to *Chem. Eur. J.* 2011, 17, 895-904.

Example 12

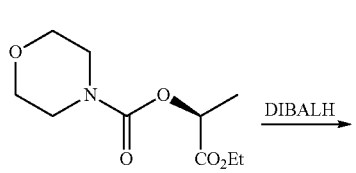

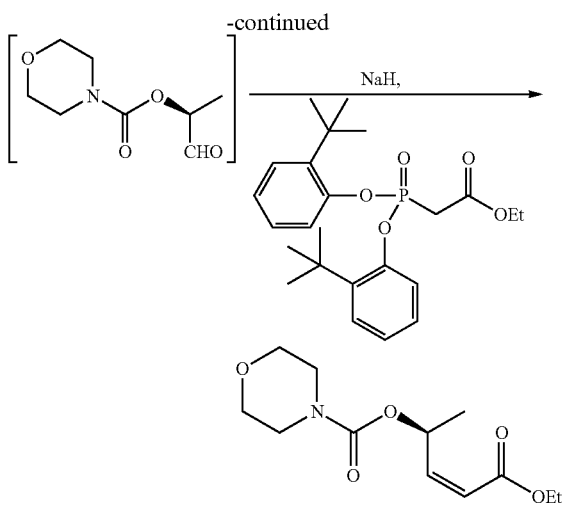

Preparation of ethyl 2-(bis(2-tert-butylphenoxy)phosphoryl)acetate:

Synthesis and spectroscopic characterization are well known in the art. For example, refer to *Chem. Eur. J.* 2011, 17, 895-904.

Example 13

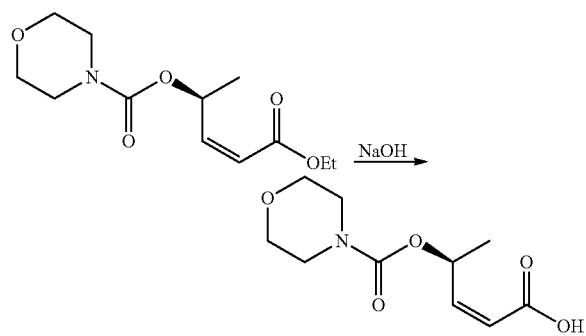

Preparation of (S,Z)-4-(morpholine-4-carbonyloxy)pent-2-enoic acid:

Synthesis and spectroscopic characterization are well known in the art. For example, refer to *Chem. Eur. J.* 2011, 17, 895-904.

Example 14

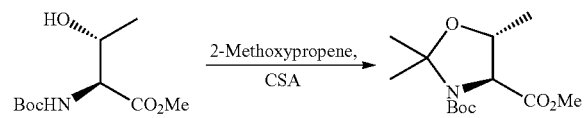

Preparation of (4S,5R)-3-tert-butyl 4-methyl 2,2,5-trimethyloxazolidine-3,4-dicarboxylate Synthesis and spectroscopic characterization are well known in the art. For example, refer to *J. Am. Chem. Soc.* 2007, 129. 2648-2659.

Example 15

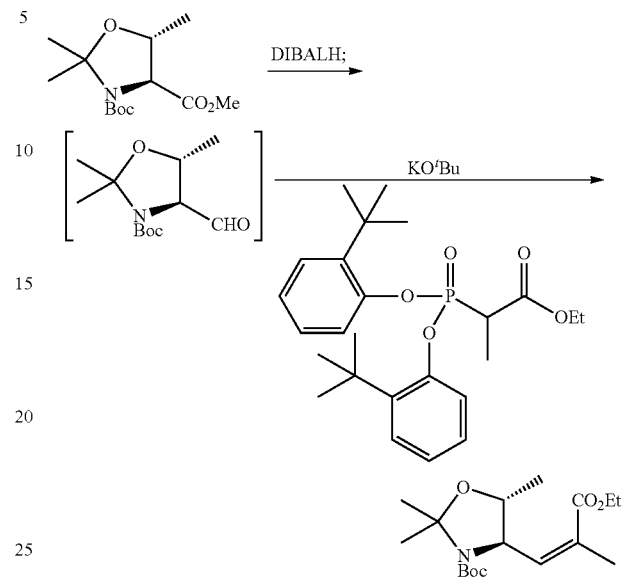

Preparation (4R,5R)-tert-butyl 4-((Z)-3-ethoxy-2-methyl-3-oxoprop-1-enyl)-2,2,5-trimethyloxazolidine-3-carboxylate: To a stirred solution of (4S,5R)-3-tert-butyl 4-methyl 2,2,5-trimethyloxazolidine-3,4-dicarboxylate (22.10 g, 49.10 mmol) in $CH_2Cl_2$ (100 mL) at −78° C. was added DIBALH (1.0 M in hexanes, 87 mL) dropwise via a syringe under a nitrogen atmosphere over 1 h. After the addition, the mixture was stirred at the same temperature for 3 h.

To a stirred solution of ethyl 2-(bis(2-tert-butylphenoxy)phosphoryl)acetate (12.3 g, 49.6 mmol) in THF at 0° C. was added KO$^t$Bu (5.06 g, 45.1 mmol) under a nitrogen atmosphere. After 20 min at the same temperature, the mixture was transferred to the solution of (4S,5R)-3-tert-butyl 4-methyl 2,2,5-trimethyloxazolidine-3,4-dicarboxylate at −78° C. by cannula. The resulting mixture was slowly warmed to 25° C. and stirred at this temperature for 45 h. The reaction mixture was quenched by adding aqueous potassium sodium tartrate (1M, 200 mL). The mixture was stirred for 30 min and extracted with EtOAc (3×250 mL). The combined organic layers were washed with brine (50 mL), dried over $Na_2SO_4$, and concentrated in vacuo. The residue was purified by flash chromatography (2 to 8% EtOAc in hexanes) on silica gel (400 mL) to afford the unsaturated ester (11.80 g, 80% yield) as a colorless oil.

Data for (4R,5R)-tert-butyl 4-((Z)-3-ethoxy-2-methyl-3-oxoprop-1-enyl)-2,2,5-trimethyloxazolidine-3-carboxylate: $R_f$=0.48 (20% EtOAc in hexanes); IR (neat): $v_{max}$=3421, 2980, 2933, 1786, 1701, 1454, 1378, 1306, 1255, 1221, 1177, 1133, 1087, 1027 cm$^{-1}$; $[\alpha]_D^{24}$ +47.6 (c 1.0, CHCl$_3$); $^1$H NMR (400 MHz, 348 K, C$_6$D$_6$): δ=5.67 (d, 1H, J=6.6 Hz), 5.08 (app t, 1H, J=7.8 Hz), 3.99 (q, 2H, J=7.2 Hz), 3.83 (qd, 1H, J=7.8, 6.6 Hz), 1.86 (s, 3H), 1.75 (s, 3H), 1.63 (s, 3H), 1.40-1.38 (m, 12H), 0.97 (t, 3H, J=7.2 Hz) ppm; $^{13}$C NMR (100 MHz, 293 K, C$_6$D$_6$): δ=167.5, 152.7, 143.2, 95.1, 79.6, 76.4, 62.7, 60.9, 29.0, 27.5, 26.5, 21.2, 19.2, 14.8 ppm; HRMS (ES+) calcd for $C_{12}H_{22}NO_3$ [(M-Boc+H)+H]$^+$ 228.1600. found 228.1603.

Example 16

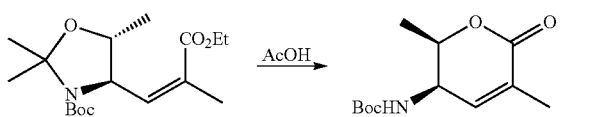

Preparation of tert-butyl (2R,3R)-2,5-dimethyl-6-oxo-3,6-dihydro-2H-pyran-3-ylcarbamate: A solution of (4R,5R)-tert-butyl 4-((Z)-3-ethoxy-2-methyl-3-oxoprop-1-enyl)-2,2,5-trimethyloxazolidine-3-carboxylate (8.80 g, 26.9 mmol) in AcOH (125 mL) was heated to 80° C. under air atmosphere. The mixture was stirred at the same temperature for 25 h. The solvent was removed in vacuo, and the residue was purified by flash chromatography (5 to 40% EtOAc in hexanes) on silica gel (300 mL) to afford the unsaturated lactone (5.00 g, 77% yield) as a white solid.

Data for tert-butyl (2R,3R)-2,5-dimethyl-6-oxo-3,6-dihydro-2H-pyran-3-ylcarbamate: m.p.=160° C.; Rf=0.38 (40% EtOAc in hexanes); IR (KBr): 3374 (N—H), 2889, 2970, 2940, 1705 (C=O), 1668, 1510, 1384, 1366, 1290, 1257, 1240, 1164 cm$^{-1}$; $[\alpha]_D^{22}$ −191.7 (c 0.5, CHCl$_3$); $^1$H NMR (300 MHz, 293 K, CDCl$_3$) 6.6.64 (dq, 1H, J=6.3, 1.4 Hz), 04.61 (dq, 1H, J=6.4, 3.1 Hz), 4.60-4.55 (m, 1H), 4.30-4.22 (m, 1H), 1.95 (dd, 3H, J=1.5, 0.9 Hz), 1.45 (s, 9H), 1.38 (d, J=6.4 Hz); $^{13}$C NMR (75 MHz, 293 K, CDCl$_3$) δ 165.3, 155.3, 138.1, 130.2, 80.2, 76.4, 46.1, 28.2, 16.9, 16.1; HRMS (EI+) calcd. for C$_8$H$_{10}$NO$_3$ (M-C$_4$H$_9$O)$^+$ 168.0661. found 168.0662.

Example 17

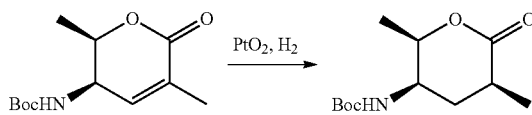

Preparation of tert-butyl (2R,3R,5S)-2,5-dimethyl-6-oxotetrahydro-2H-pyran-3-ylcarbamate: Synthesis and characterization via spectroscopic data of tert-butyl (2R,3R,5S)-2,5-dimethyl-6-oxotetrahydro-2H-pyran-3-ylcarbamate is well known in the art. For a detailed protocol refer to *J. Am. Chem. Soc.* 2007, 129. 2648-2659.

Example 18

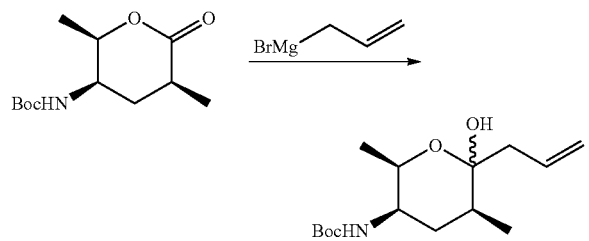

Preparation of tert-butyl (2R,3R,5S)-6-allyl-6-hydroxy-2,5-dimethyltetrahydro-2H-pyran-3-ylcarbamate: Synthesis and characterization via spectroscopic data of tert-butyl (2R,3R,5S)-6-allyl-6-hydroxy-2,5-dimethyltetrahydro-2H-pyran-3-ylcarbamate is well known in the art. For a detailed protocol refer to *J. Am. Chem. Soc.* 2007, 129. 2648-2659.

Example 19

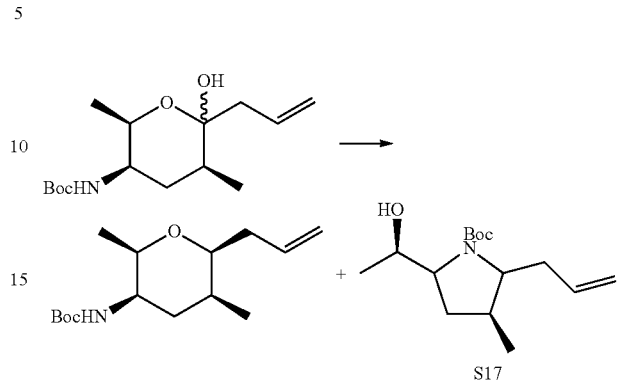

Preparation of tert-butyl (2R,3R,5S,6S)-6-allyl-2,5-dimethyltetrahydro-2H-pyran-3-ylcarbamate: Synthesis and characterization via spectroscopic data of tert-butyl (2R,3R,5S,6S)-6-allyl-2,5-dimethyltetrahydro-2H-pyran-3-ylcarbamate is well known in the art. For a detailed protocol refer to *J. Am. Chem. Soc.* 2007, 129. 2648-2659.

Example 20

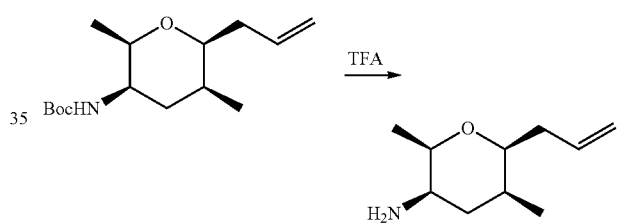

Preparation of (2R,3R,5S,6S)-6-allyl-2,5-dimethyltetrahydro-2H-pyran-3-amine: Synthesis and characterization via spectroscopic data of tert(2R,3R,5S,6S)-6-allyl-2,5-dimethyltetrahydro-2H-pyran-3-amine is well known in the art. For a detailed protocol refer to *J. Am. Chem. Soc.* 2007, 129. 2648-2659.

Example 21

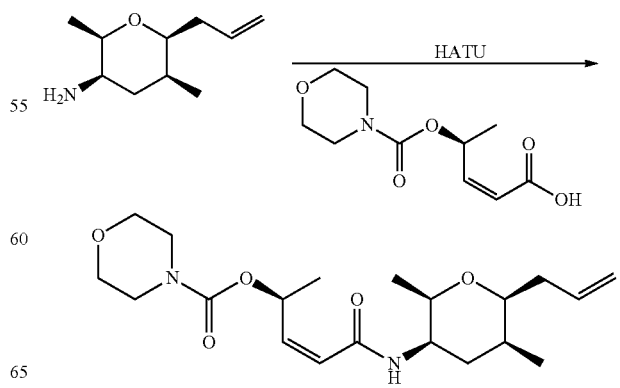

Preparation of (S,Z)-5-((2R,3R,5S,6S)-6-allyl-2,5-dimethyltetrahydro-2H-pyran-3-ylamino)-5-oxopent-3-en-2-yl morpholine-4-carboxylate: An oven-dried, 50-mL, single-necked, round-bottomed flask equipped with a Teflon-coated magnetic stir bar, a rubber septum and a nitrogen inlet was charged with (S,Z)-4-(morpholine-4-carbonyloxy)pent-2-enoic acid (270 mg, 1.70 mmol), MeCN (6 mL) and O-(7-azabenzotriazol-1-yl)-N,N,N',N'-tetramethyluronium hexafluorophosphate (646 mg, 1.70 mmol), followed by N,N'-diisopropylethylamine (0.990 mL, 5.68 mmol) via a syringe. The resulting mixture was stirred at 23° C. for 5 min and then added to the solution of (2R,3R,5S,6S)-6-allyl-2,5-dimethyltetrahydro-2H-pyran-3-amine in MeCN prepared in the last step. The resulting pale yellow solution was stirred 23° C. for 20 min. Water (7 mL) was added, and the mixture was extracted with EtOAc (3×20 mL). The combined organic layers were washed with brine (20 mL), dried over anhydrous $Na_2SO_4$, filtered, and concentrated in vacuo. The crude residue was purified by flash chromatography (10 to 50% EtOAc in hexanes) on silica gel (30 mL) to afford the alkene (265 mg, 66% yield) as a colorless oil.

Example 22

Example 23

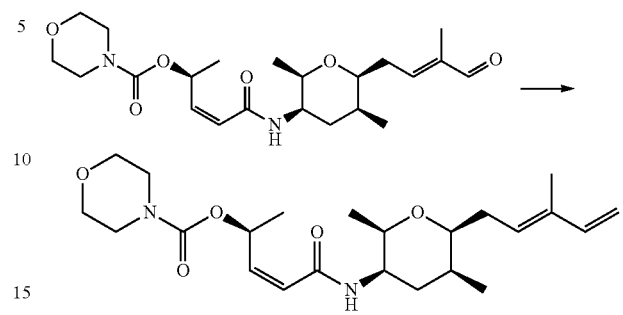

Preparation of (S,Z)-5-((2R,3R,5S,6S)-2,5-dimethyl-6-((E)-3-methylpenta-2,4-dienyl)tetrahydro-2H-pyran-3-ylamino)-5-oxopent-3-en-2-yl morpholine-4-carboxylate: An oven-dried, 50-mL, single-necked, round-bottomed flask equipped with a Teflon-coated magnetic stir bar, a rubber septum and a nitrogen inlet was charged with methyltriphenylphosphonium bromide (803 mg, 2.25 mmol) and THF (8 mL). The solution was cooled in an ice-water bath, and a solution of KO$^t$Bu in THF (1M, 1.90 mL, 1.90 mmol) was

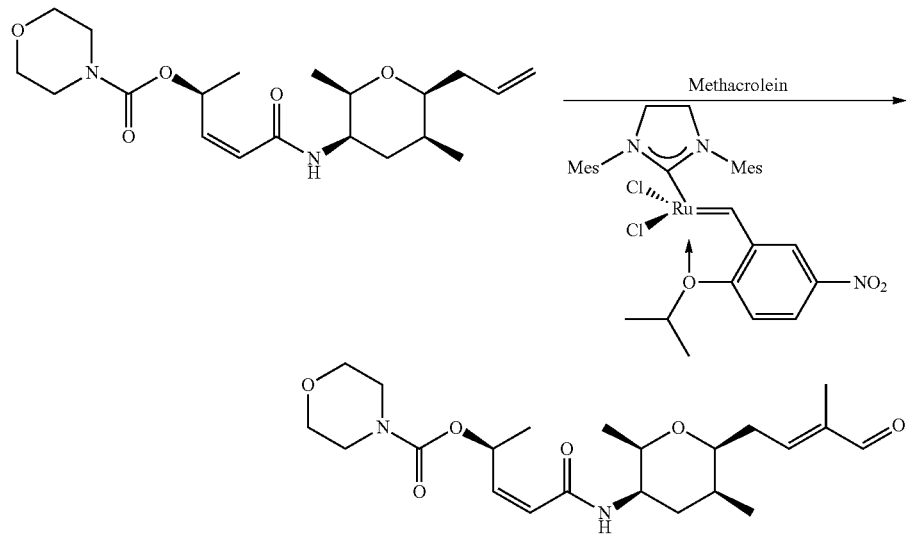

Preparation of (S,Z)-5-((2R,3R,5S,6S)-2,5-dimethyl-6-((E)-3-methyl-4-oxobut-2-enyl)tetrahydro-2H-pyran-3-ylamino)-5-oxopent-3-en-2-yl morpholine-4-carboxylate: A 10-mL, single-necked, round-bottomed flask equipped with a Teflon-coated magnetic stir bar, a nitrogen inlet and a rubber septum was charged with (S,Z)-5-((2R,3R,5S,6S)-6-allyl-2,5-dimethyltetrahydro-2H-pyran-3-ylamino)-5-oxopent-3-en-2-yl morpholine-4-carboxylate (0.27 g, 0.95 mmol), methacrolein (1.2 mL, 14 mmol) and Nitro-Grela Grubbs catalyst (6.3 mg, 9.4 µmol). The resulting mixture was stirred at 23° C. for 22 h, and additional Nitro-Grela Grubbs catalyst (6.3 mg, 9.4 µmol) was added. The stirring was continued for 13 h and the mixture was concentrated in vacuo. The residue was purified by flash chromatography (30 to 80% EtOAc in hexanes) on silica gel (15 mL) to afford the aldehyde (185 mg, 60%) as a colorless oil.

added via a syringe. The mixture was stirred for 10 min at the same temperature. A solution of (S,Z)-5-((2R,3R,5S,6S)-2,5-dimethyl-6-((E)-3-methyl-4-oxobut-2-enyl)tetrahydro-2H-pyran-3-ylamino)-5-oxopent-3-en-2-yl morpholine-4-carboxylate (183 mg, 0.566 mmol) in THF (7 mL) was added to the mixture via cannula, and the stirring was continued for 10 min. $H_2O$ (5 mL) was added. After removal of THF, the mixture was extracted with EtOAc (3×20 mL). The combined organic layers were washed with brine (20 mL), dried over anhydrous $Na_2SO_4$, filtered and concentrated in vacuo. The crude residue was purified by flash chromatography (10 to 50% EtOAc in hexanes) on silica gel (20 mL) to afford the diene (124 mg, 69% yield) as a colorless oil.

Data for (S,Z)-5-((2R,3R,5S,6S)-2,5-dimethyl-6-((E)-3-methylpenta-2,4-dienyl)tetrahydro-2H-pyran-3-ylamino)-5-oxopent-3-en-2-ylmorpholine-4-carboxylate: Rf=0.47 (80%

EtOAc in hexanes); IR (film): 3360, 2962, 2922, 2853, 1702 (C=O), 1669 (C=O), 1639, 1517, 1424, 1241, 1118, 1072 cm$^{-1}$; $[\alpha]_D^{26}$ −6.7 (c 0.60, CH$_2$Cl$_2$); $^1$H NMR (500 MHz, 293K, CD$_2$Cl$_2$) δ 6.37 (dd, 1H, J=17.5, 10.5 Hz), 6.17-6.12 (m, 2H), 5.91 (dd, 1H, J=11.5, 8.0 Hz), 5.70 (dd, 1H, J=11.5, 1.5 Hz), 5.50 (app t, 1H, J=7.0 Hz), 5.11 (d, 1H, J=17.5 Hz), 4.94 (d, 1H, J=11.5 Hz), 3.92-3.89 (m, 1H), 3.66 (qd, 1H, J=6.5, 2.0 Hz), 3.61 (app t, 4H, J=4.5 Hz), 3.54 (ddd, 1H, J=9.5, 7.0, 3.0 Hz), 3.42 (app t, 4H, J=4.5 Hz), 2.39-2.33 (m, 1H), 2.25-2.19 (m, 1H), 1.95-1.92 (m, 2H), 1.79-1.76 (m, 1H), 1.75 (s, 3H), 1.35 (d, 3H, J=6.5 Hz), 1.12 (d, 3H, J=6.5 Hz), 1.03 (d, 3H, J=7.5 Hz); $^{13}$C NMR (125 MHz, 293 K, CD$_2$Cl$_2$) δ 165.3, 155.4, 144.4, 141.9, 136.0, 129.4, 122.8, 111.2, 81.3, 76.4, 70.1, 67.1, 47.6, 36.4, 32.5, 30.3, 29.7, 20.6, 18.1, 15.4, 12.2; HRMS (ESI+) calcd. for C$_{23}$H$_{36}$N$_2$O$_5$ [M+Na]$^+$ 443.2522. found 443.2496.

Example 24

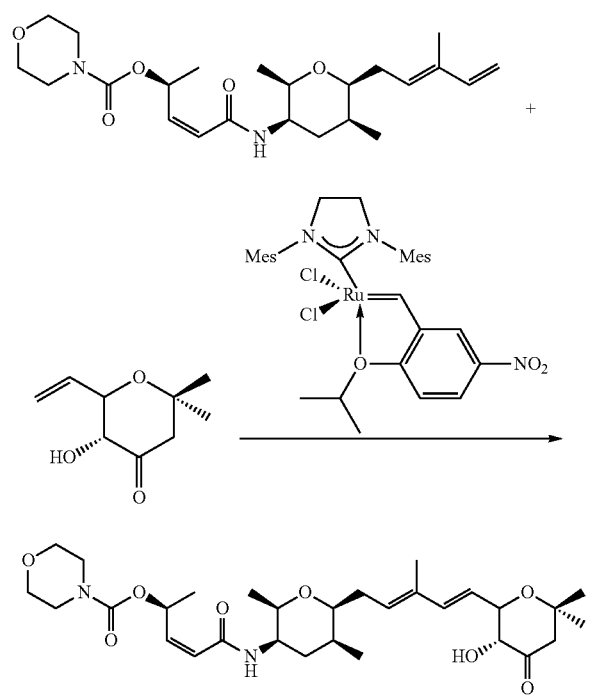

Preparation of (S,Z)-5-((2R,3R,5S,6S)-6-((2E,4E)-5-((2R,3R)-3-hydroxy-6,6-dimethyl-4-oxotetrahydro-2H-pyran-2-yl)-3-methylpenta-2,4-dienyl)-2,5-dimethyltetrahydro-2H-pyran-3-ylamino)-5-oxopent-3-en-2-yl morpholine-4-carboxylate: A 10-mL round-bottomed flask equipped with equipped with a Teflon-coated magnetic stir bar containing (S,Z)-5-((2R,3R,5S,6S)-2,5-dimethyl-6-((E)-3-methylpenta-2,4-dienyl)tetrahydro-2H-pyran-3-ylamino)-5-oxopent-3-en-2-yl morpholine-4-carboxylate (18 mg, 0.04 mmol) and (5R,6R)-5-hydroxy-2,2-dimethyl-6-vinyldihydro-2H-pyran-4(3H)-one (9.1 mg, 0.05 mmol) was charged with DCE (0.3 mL), nitro Grela-Grubbs catalyst (3.2 mg, 0048 mmol). The mixture was stirred in an oil bath for 2 h at 40° C., then additional nitro Grela-Grubbs catalyst (2.1 mg, 0.0031 mmol) was added, and the mixture was stirred for an additional 14 h, then concentrated in vacuo. The crude residue was purified by flash chromatography (10→100% EtOAc in hexanes) on silica gel (5 mL) to afford the product as an oil (8.1 mg, 36% yield). Some of this material was purified by preparative-TLC (EtOAc) and used for biological experiments.

Data for (S,Z)-5-((2R,3R,5S,6S)-6-((2E,4E)-5-((2R,3R)-3-hydroxy-6,6-dimethyl-4-oxotetrahydro-2H-pyran-2-yl)-3-methylpenta-2,4-dienyl)-2,5-dimethyltetrahydro-2H-pyran-3-ylamino)-5-oxopent-3-en-2-ylmorpholine-4-carboxylate: R$_f$=0.26 (70% EtOAc in hexanes); IR (film): ν$_{max}$=3341 (br, O—H), 2973, 2923, 1734 (C=O), 1668 (C=O), 1526, 1372, 1243, 1130, 1 cm$^{-1}$; $[\alpha]_D^{19}$ +2.16 (c 0.74, CH$_2$Cl$_2$); $^1$H NMR (500 MHz, 1% CD$_3$OD in CDCl$_3$, 293 K): δ=6.43 (d, J=16.0 Hz, 1, 7-H), 6.20 (br d, J=9.0 Hz, 1H, N—H), 6.17-6.13 (m, 1H, 4'-H), 5.94 (dd, J=12.0, 7.5 Hz, 1H, 3'-H), 5.74 (dd, J=12.0, 1.0 Hz, 1H, 2'-H), 5.58 (dd, J=16.0, 9.0 Hz, 1H, 6-H), 5.36-5.30 (m, 1H, 9-H), 4.16 (dd, J=9.0, 9.0 Hz, 1H, 4-H), 3.97-3.95 (m, 2H, 5-H, 14-H), 3.68-3.65 (m, 4H, CH$_2$O), 3.60-3.52 (m, 2H, 15-H, 11-H), 3.50-3.48 (m, 4H, CH$_2$N), 2.42-2.38 (m, 2H, 10-H, 2$_{axial}$-H), 2.26-2.23 (m, 1H, 10-H), 1.98-1.93 (m, 2H, 13-H), 1.88 (d, J=14.0 Hz, 1H, 2$_{equatorial}$-H), 1.80 (s, 3H, 19-H), 1.78-1.76 (m, 1H, 12-H), 1.48 (s, 3H, 17-H), 1.43 (d, J=6.5 Hz, 3H, 4'-H), 1.28 (s, 3H, 17'-H), 1.17 (d, J=6.5 Hz, 3H, 16-H), 1.04 (d, J=7.5 Hz, 3H, 20-H); $^{13}$C NMR (100 MHz, CD$_2$Cl$_2$, 293 K): δ=208.2, 164.4, 154.3, 142.7, 136.5, 135.0, 131.5, 125.1, 123.2, 83.6, 75.7, 73.8, 70.1, 66.6, 57.3, 47.0, 44.4, 35.8, 34.6, 31.6, 29.7, 22.7, 20.0, 17.4, 15.2, 13.9; HRMS (ESI+) calcd. for C$_{30}$H$_{46}$N$_2$O$_8$Na [M+Na]$^+$ 585.3152. found 585.3157.

Example 25

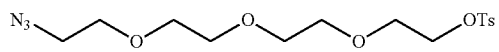 [SMILES: Cc1ccc(S(=O)(=O)OCCOCCOCCOCCN=[N+]=[N-])cc1]

Synthesis of 2-(2-(2-(2-azidoethoxyl)ethoxy)ethoxy)ethyl 4-methylbenzenesulfonate: Synthesis of 2-(2-(2-(2-azidoethoxyl)ethoxy)ethoxy)ethyl 4-methylbenzenesulfonate is well known in the art. For a detailed protocol, see H. S. Gill, et. al. *J. Med. Chem.*, 2009, 52, 5816-5825.

Example 26

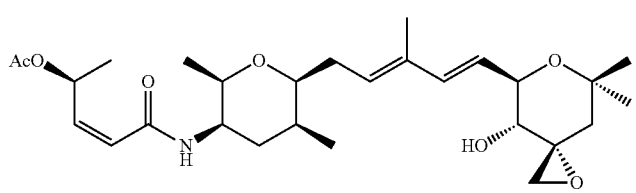

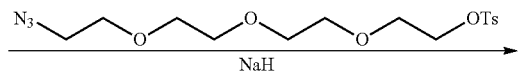

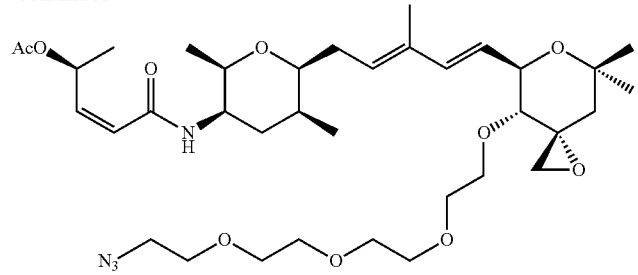

Preparation of 4-TEGylated meayamycin: A 10-mL round-bottomed flask equipped with a Teflon-coated magnetic stir bar containing meayamycin (3.3 mg, 0.0065 mmol) was added THF (0.1 mL) and 2-(2-(2-(2-azidoethoxyl)ethoxy)ethoxy)ethyl 4-methylbenzenesulfonate (7.1 mg, 2.8 mmol). The flask was cooled in an ice-water bath (0° C. external temperature), then NaH (5.3 mg, 0.13 mmol) was added to the flask. The mixture was stirred for 7 h as the ice-water bath was left to warm to 23° C. The mixture was diluted with saturated aqueous NH$_4$Cl (2 mL), and THF was removed in vacuo. The resulting mixture was extracted with EtOAc (6×5 mL). The combined organic layers were dried over Na$_2$SO$_4$, filtered and concentrated in vacuo. The residue was purified by preparative-TLC (80% EtOAc in hexanes) to afford 4-TEGylated meayamycin as a colorless oil (2.3 mg, 51% yield).

Data for 4-TEGylated meayamycin: $R_f$=0.23 (80% EtOAc in hexanes); IR (film): $v_{max}$=3391, 2922, 2854, 2106 (N$_3$), 1779 (C=O), 1598 (C=O), 1459, 1178, 1017 cm$^{-1}$; $[\alpha]_D^{22}$ +10.2 (c 0.23, CH$_2$Cl$_2$); $^1$H NMR (500 MHz, CDCl$_3$, 293 K): δ=6.40 (d, J=15.5 Hz, 1H, 7-H), 6.27 (m, 4'-H), 5.99 (br d, J=9.0 Hz, 1H, N—H), 5.90 (dd, J=11.5, 7.5 Hz, 1H, 3'-H), 5.71 (dd, J=11.5, 1.5 Hz, 1H, 2'-H), 5.64 (dd, J=15.5, 7.5 Hz, 1H, 6-H), 5.48 (br t, J=7.5 Hz, 1H, 9-H), 4.26 (dd, J=9.0, 7.5 Hz, 1H, 5-H), 3.97-3.93 (m, 1H, 14-H), 3.72-3.48 (m, 16H, tetraethylene glycol-H's, 15-H, 11-H), 3.42-3.39 (m, 2H, N$_3$CH$_2$), 3.32 (d, J=9.0 Hz, 1H, 4-H), 3.12 (d, J=5.5 Hz, 1H, 18-H), 2.45 (d, J=5.5 Hz, 1H, 18-H), 2.42-2.39 (m, 1H, 10-H), 2.24-2.21 (m, 1H, 10-H), 2.13 (d, J=14.0 Hz, 1H, 2$_{axial}$-H), 2.07 (s, 3H, 2''-H), 1.99-1.94 (m, 2H, 13-H), 1.78 (s, 3H, 19-H), 1.62-1.59 (m, 1H, 12-H), 1.43 (s, 3H, 17-H), 1.40 (d, J=6.5 Hz, 3H, 5'-H), 1.39 (d, J=14.0 Hz, 1H, 2$_{equatorial}$-H), 1.28 (s, 3H, 17'-H), 1.16 (d, J=6.5 Hz, 3H, 16-H), 1.02 (d, J=7.5 Hz, 3H, 20-H); $^{13}$C NMR (125 MHz, CDCl$_3$, 293 K): δ=170.4, 164.8, 143.5, 138.1, 134.7, 125.0, 122.5, 80.8, 77.5, 75.9, 74.6, 72.9, 70.7, 70.6, 70.1, 68.9, 68.1, 57.5, 50.7, 47.6, 47.1, 42.8, 35.8, 31.9, 31.0, 28.9, 23.6, 21.3, 20.0, 17.8, 15.4, 12.8; HRMS (ESI+) calcd. for C$_{36}$H$_{58}$N$_4$O$_{10}$Na [M+Na]$^+$ 729.4051. found 729.4031.

Example 27

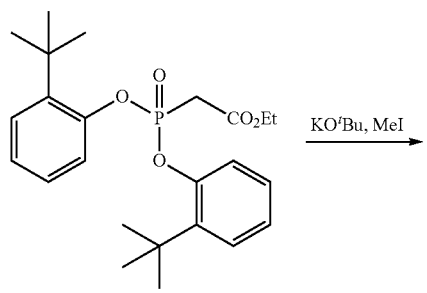 → KO$^t$Bu, MeI

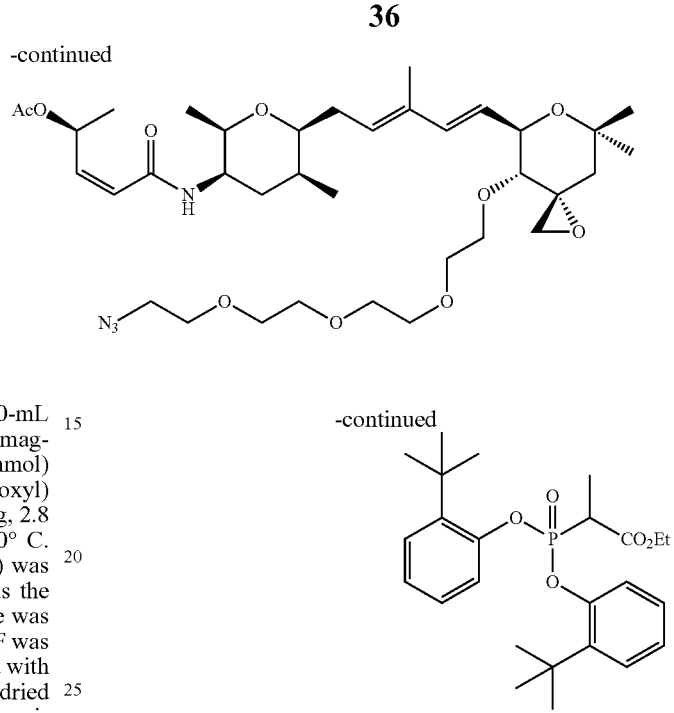

Preparation of ethyl 2-(bis(2-tert-butylphenoxy)phosphoryl)propanoate:

Ethyl 2-(bis(2-tert-butylphenoxy)phosphoryl)acetate (50.01 g, 115.6 mmol) was added to an oven-dried 500-mL single-necked round-bottomed flask that had been flushed with nitrogen and equipped with a Teflon-coated magnetic stir bar. The flask was resealed with a rubber septum fitted with a nitrogen inlet. THF (140 mL) was added to this flask, and the resulting solution was cooled to 0° C. in an ice water bath. The solution was then treated with potassium tert-butoxide (19.46 g, 173.5 mmol) and stirred at 0° C. for 5 min, then allowed to warm to 23° C. After 2 h the solution was cooled to 0° C. in an ice water bath and iodomethane (10.7 mL, 173 mmol) was added via syringe. The resulting solution was allowed to warm to 23° C., and stirred for 2 h. The resulting mixture was treated with saturated aqueous NH$_4$Cl (100 mL) at 23° C. The quenched mixture was then extracted with EtOAc (3×100 mL), dried over anhydrous Na$_2$SO$_4$, filtered, and concentrated in vacuo. The crude residue was purified by recrystallization from boiling hexanes (30 mL) and cooled to −20° C. to give 33.56 g (65% yield) of ethyl 2-(bis(2-tert-butylphenoxy)phosphoryl)propanoate as a white solid.

Data for ethyl 2-(bis(2-tert-butylphenoxy)phosphoryl)propanoate: $R_f$=0.34 (20% EtOAc in hexanes); IR (neat): $v_{max}$=3391, 3032, 2958, 1738, 1672, 1488, 1442, 1300, 1257, 1180, 1086, 1056, 938, 757 cm$^{-1}$; $^1$H NMR (400 MHz, 293K, CDCl$_3$): δ=7.74 (d, 1H, J=8.0 Hz), 7.65 (d, 1H, J=8.0 Hz), 7.36 (dd, 2H, J=7.6, 1.6 Hz), 7.12-7.04 (m, 4H), 4.19-4.11 (dq, 1H, J=10.8, 7.2 Hz), 4.05-3.97 (dq, 1H, J=10.8, 7.2 Hz), 3.54-3.43 (dq, 1H, J=22.8, 7.2 Hz), 1.73-1.66 (dd, 3H, J=19.6, 7.2 Hz), 1.36 (s, 9H), 1.32 (s, 9H), 1.11 (t, 3H, J=7.2 Hz) ppm; $^{13}$C NMR (100 MHz, 293K, CDCl$_3$): 168.4, 168.3, 150.9, 150.8, 150.6, 150.5, 138.9, 138.8, 138.7, 138.69, 127.5, 127.4, 127.3, 127.28, 127.2, 124.33, 124.3, 124.1, 119.7, 119.69, 119.5, 119.48, 61.9, 41.94, 41.9, 40.1, 34.6, 30.1, 29.98, 13.8, 12.0, 11.9 ppm; HRMS (ES+) calcd for C$_{25}$H$_{35}$O$_5$P [M+H]$^+$ 447.2300. found 447.2305.

Separation of ethyl 2-(bis(2-tert-butylphenoxy)phosphoryl)propanoate from ethyl 2-(bis(2-tert-butylphenoxy)phosphoryl)acetate: A 1:1.11 (18.9 g) mixture of ethyl 2-(bis(2-tert-butylphenoxy)phosphoryl)propanoate and ethyl 2-(bis(2-tert-butylphenoxy)phosphoryl)acetate was added to an oven-dried 500-mL single-necked round bottom flask that had been flushed with nitrogen and equipped with a Teflon-coated magnetic stir bar. The flask was resealed with a rubber septum fitted with a nitrogen inlet. THF (200 mL) was added and flask cooled in an ethylene glycol/dry ice bath. Potassium tert-butoxide was added at −20° C. and stirred at the same temperature for 10 min, then PhCHO (2.3 mL, 0.55 equiv) was added via syringe. Stirred for 2 h at −20° C. The resulting mixture was treated with 50 mL saturated aqueous $NH_4Cl$ and extracted with EtOAc (3×75 mL), the combined organic layers washed with brine, dried over anhydrous $Na_2SO_4$ and concentrated in vaccuo to afford a pale yellow oil that was recrystallized from boiling hexanes and cooled to −20° C. to give 8.06 g (44% yield) ethyl 2-(bis(2-tert-butylphenoxy)phosphoryl)propanoate as a white solid.

Example 28

Synthesis of an FR901464 analog (4-TEGylated FR901464): Synthesis of a 4-TEGylated analog of FR901464 was synthesized according to the following scheme. Detailed protocols for synthesis of intermediates is found in previous examples.

Preparation of (S,Z)-5-((2R,3R,5S,6S)-2,5-dimethyl-6-((E)-3-methylpenta-2,4-dienyl)tetrahydro-2H-pyran-3-ylamino)-5-oxopent-3-en-2-yl morpholine-4-carboxylate

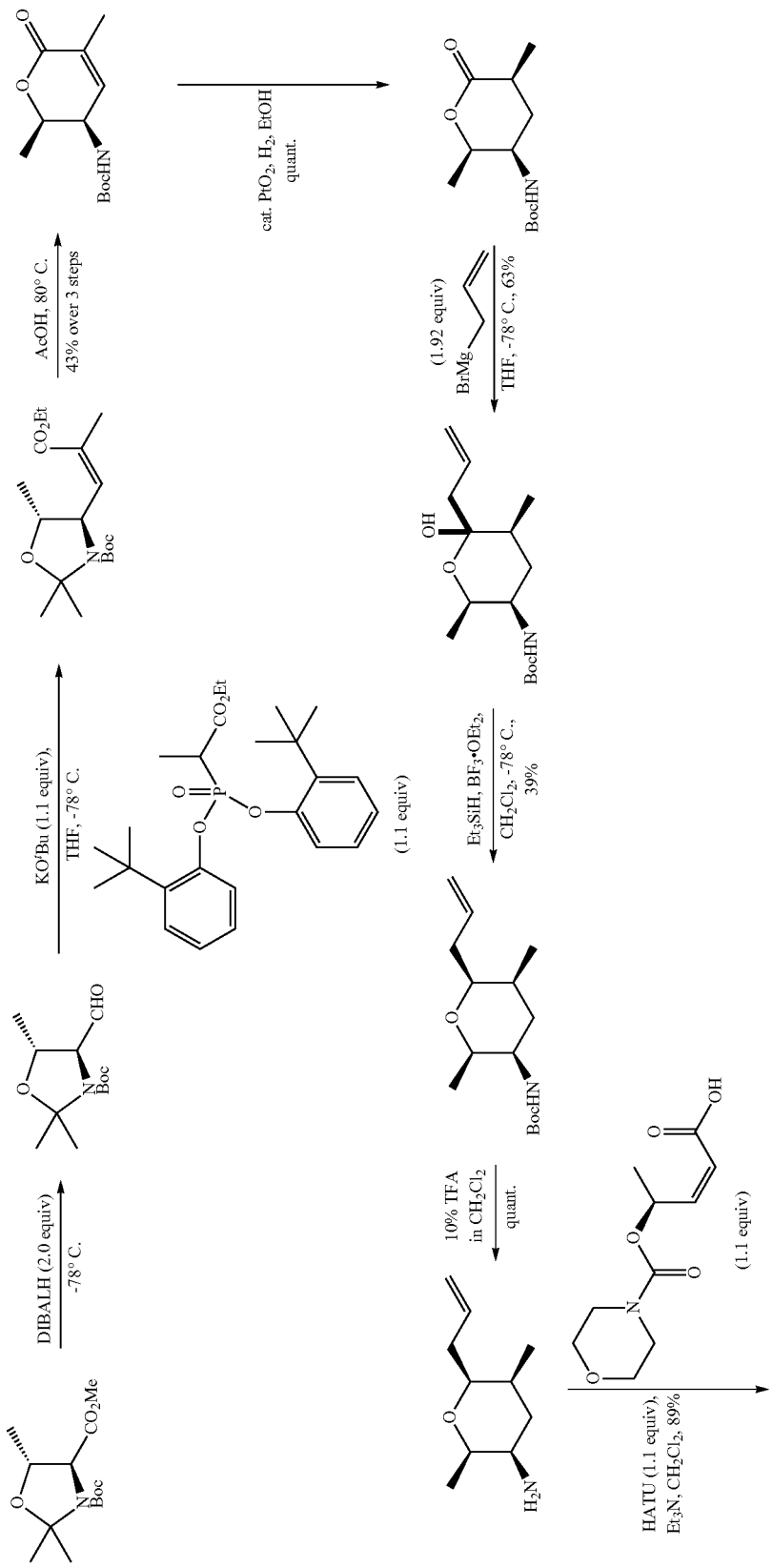

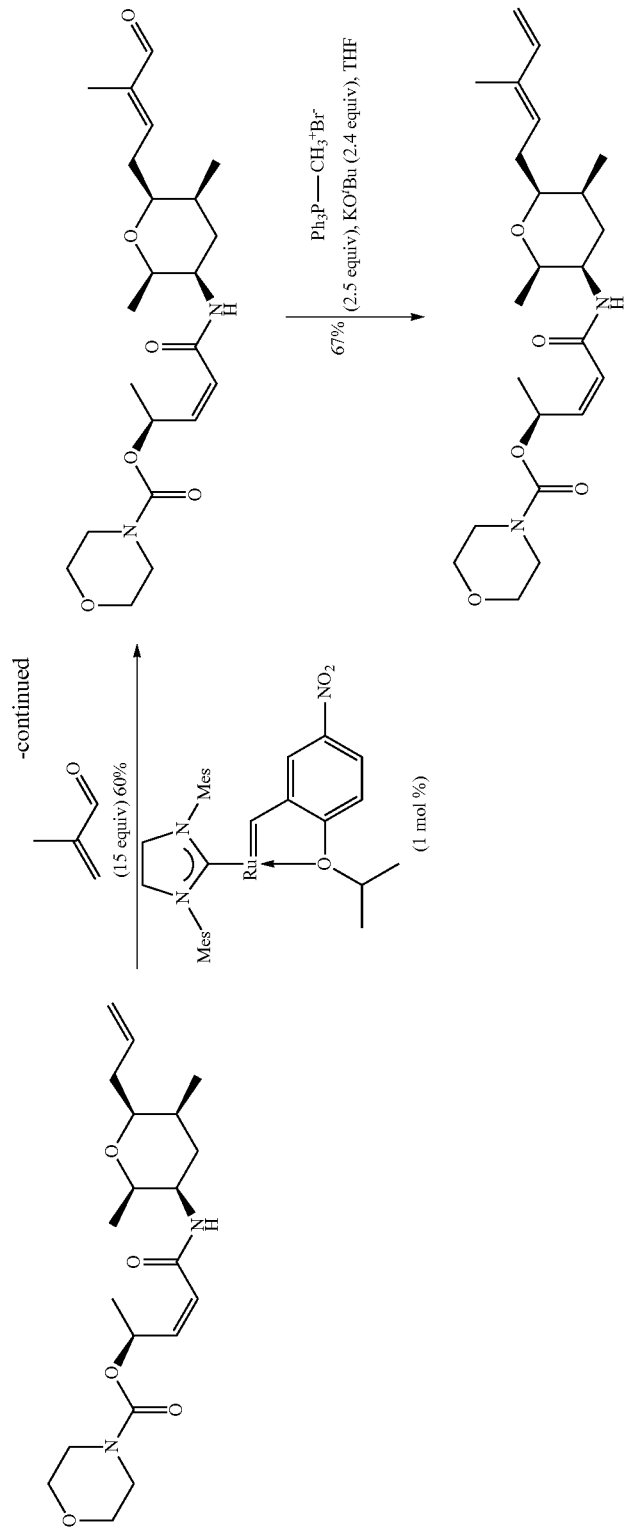

Preparation of (3R,4R,5R)-7,7-dimethyl-5-vinyl-1,6-dioxaspiro[2.5]octan-4-ol

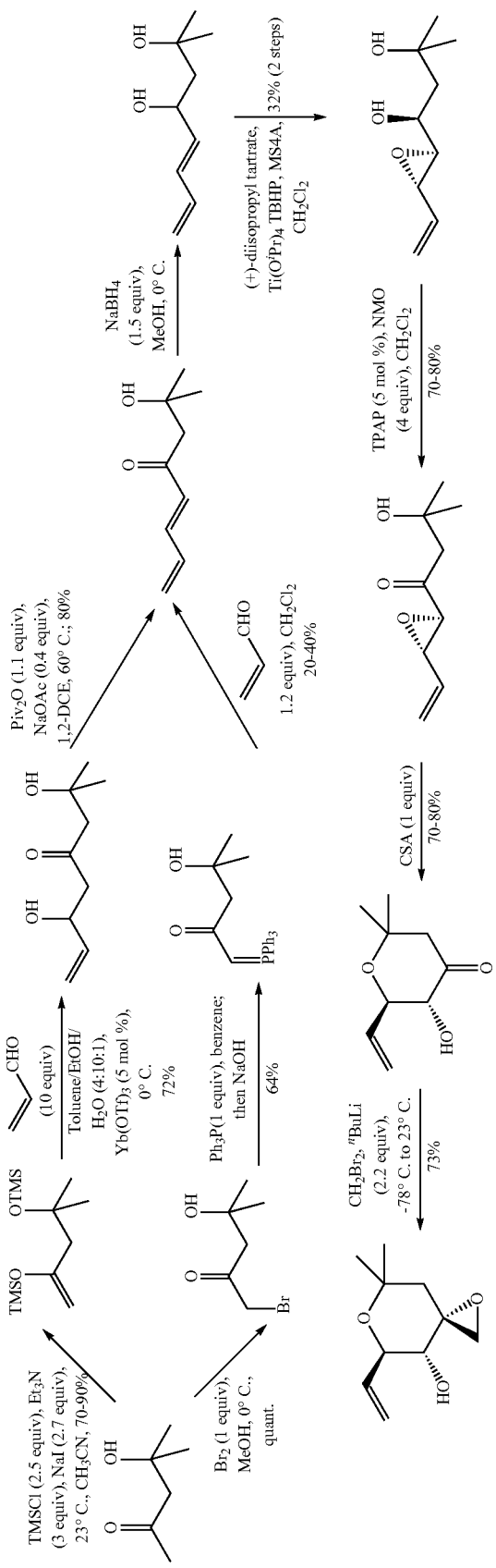

Preparation of 4-TEGylated FR901464 from (S,Z)-5-((2R,3R,5S,6S)-2,5-dimethyl-6-((E)-3-methylpenta-2,4-dienyl)tetrahydro-2H-pyran-3-ylamino)-5-oxopent-3-en-2-yl morpholine-4-carboxylate and (3R,4R,5R)-7,7-dimethyl-5-vinyl-1,6-dioxaspiro[2.5]octan-4-ol:

Growth Inhibition Assay

Cells were plated in 96 well plates at an initial density of 2,000 cells per well in 100 µL of medium and were incubated for 24 hours prior to compound addition. Serial two-fold dilutions were used in this experiment from 100

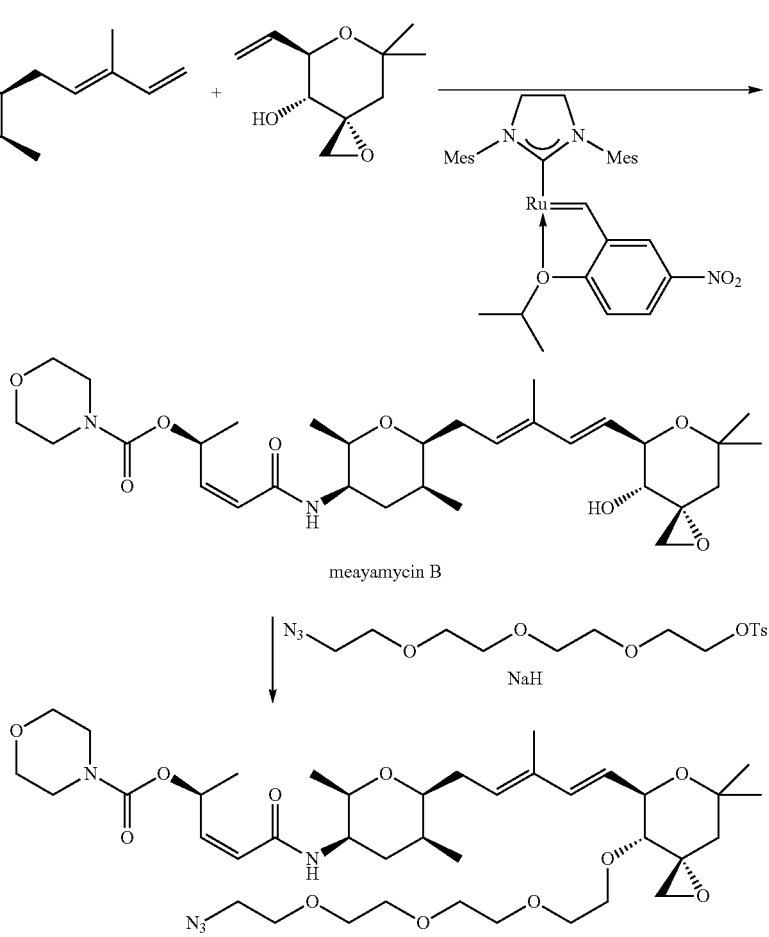

meayamycin B

Example 29

Inhibition Assays

The purpose of this example was to observe the antiproliferative activity of meayamycin, 4-TEGylated meayamycin, and 4-TEGylated meayamycin (right fragment) on various cancer cell lines.

Materials

Meayamycin, 4-TEGylated meayamycin, and 4-TEGylated FR901464 (right fragment) compounds were produced using the above protocols. The compounds were dissolved in dimethyl sulfoxide (DMSO) as 10 mM stocks and stored at −20° C. Prior to assays being performed, aliquots were thawed at room temperature and dilutions were prepared in RPMI 1640 medium containing 2% DMSO at 2×the desired concentration prior to addition to the cells.

Cell Culture

The cells were grown at 37° C. in an atmosphere containing 5% carbon dioxide in corning cell culture flasks (25 cm$^2$) in RPMI 1640 cell culture medium containing 10% fetal bovine serum, 1% Penicillin/Streptomycin, and 1% L-Glutamine.

nM to 0.000191 nM. The compound was added to the cells at 2× the desired concentration in 100 µL cell culture medium. The cells were then incubated for an additional 3 to 5 days. Cell proliferation was measured using a commercial MTS solution (20 µL per well). The absorbance (at 490 nm and 630 nm) was measured by a Spectromax M2 plate reader (Molecular Devices). Each concentration treatment was done in quadruplets and the final numbers were averaged.

Reversibility Tests

Cells were plated in 96 well plates at an initial density of 2,000 cells per well in 100 µL of medium and were incubated for 24 hours prior to compound addition. One concentration was used in each experiment for all times examined. The compound was added to the cells at 2× the desired concentration in 100 µL cell culture medium. At the desired time intervals, the media containing the drug was removed, the wells were washed 5 times with new media and 200 µL of new media containing 1% DMSO was added. At the last time interval, after washing and replacing the media, cell proliferation was measured using a commercial MTS solution (20 µL per well). The absorbance (at 490 nm and 630 nm) was measured by a Spectromax M2 plate reader (Molecular Devices). Each concentration treatment was done in quadruplets and the final numbers were averaged.

Results

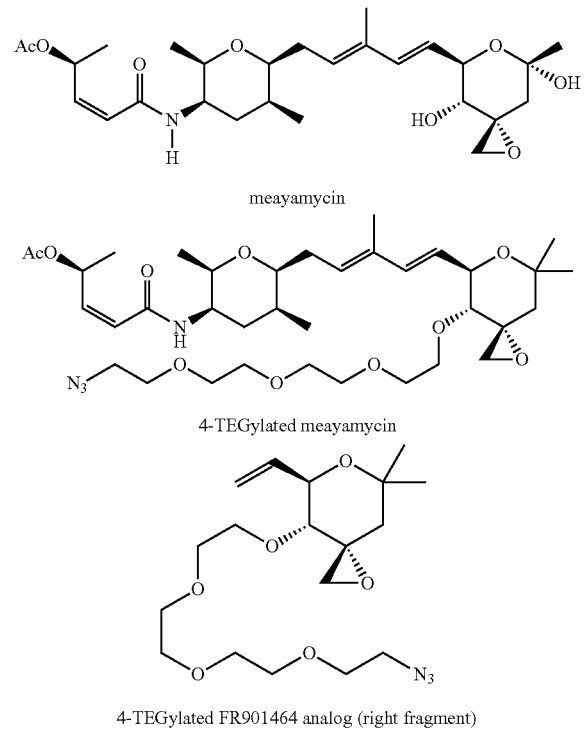

meayamycin

4-TEGylated meayamycin

4-TEGylated FR901464 analog (right fragment)

The $GI_{50}$ values (in nM) of meayamycin and its analogs are summarized below.

|  | MCF-7 | A549 | JHU 012 | HCT116 | MDA-MB-231 | HEK-293-II | PCI 13 |
|---|---|---|---|---|---|---|---|
| meayamycin | 0.80 | 0.26 | 4.7 | 0.038 | 0.070 | 7.8 | 4.8 |
| 4-TEGylated meayamycin | 2.4 |  |  | 0.10 |  | 46 |  |
| 4-TEGylated FR901464 (right fragment) |  | $2.2 \times 10^3$ | $2.0 \times 10^3$ | $2.2 \times 10^3$ | $1.5 \times 10^3$ | $8.9 \times 10^3$ | $3.7 \times 10^3$ |

Example 30

Splicing Inhibition

Figure 2:
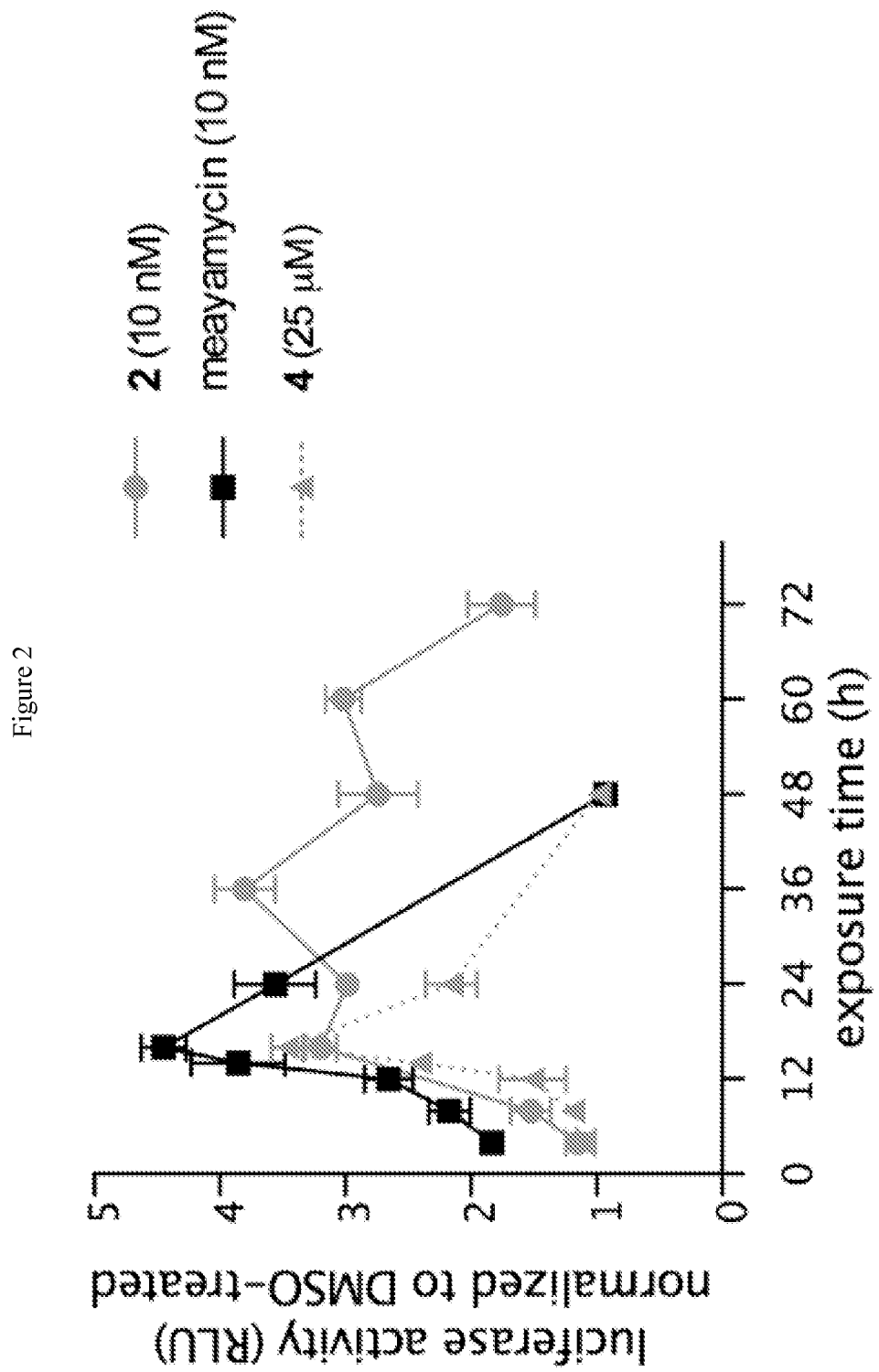
FIG. 2 is a graph that compares luciferase activity versus time for HEK-293-II cells treated with 4-TEGylated meayamycin, meayamycin, and 4-TEGylated FR901464 (right fragment).

Splicing inhibition by PEGylated meayamycin was evaluated using the published HEK-293-II cell-based assay. In short, luciferase expression increases when pre-mRNA splicing is inhibited. Yang Gao et al., published online at *Chem Bio Chem.* Nov. 22, 2012 (DOI: 10.1002/cbic.201200558). In this assay, PEGylated meayamycin exhibited a dose-dependent inhibitory activity towards pre-mRNA splicing after 16-h treatment ($IC_{150}$=2.4 nM; average of three independent experiments). The RT-PCR analysis of the total RNA extracted from 4-TEGylated meayamycin-, meayamycin- and DMSO-treated cells further validated that the analogue 4-TEGylated meayamycin inhibited pre-mRNA splicing. (FIG. 1). Pre-mRNA splicing inhibition by 4-TEGylated meayamycin was examined in HEK-293-II cells over 72 h. The splicing inhibition, as manifested by the luciferase activity, in the 4-TEGylated meayamycin-treated cells persisted for 48 h, which was different from that in the meayamycin-treated cells. (FIG. 2). Because others have used meayamycin and related compounds to study pre-mRNA splicing over time, the availability of distinctly temporal splicing inhibitors may prove useful in such mechanistic studies.

To further investigate the effect of the PEG-$N_3$ chain on the 4-hydroxy group of meayamycin, we installed the same PEG-$N_3$ chain on the corresponding hydroxyl group of the right fragment. The PEGylated right fragment was found to inhibit HCT-116 proliferation with a $GI_{150}$ of 1.5 µM. The right fragment without PEGylation exhibited no antiproliferation activity even at 200 µM.

We claim:

1. A compound having Formula I or a stereoisomer, pharmaceutically acceptable salt or ester thereof:

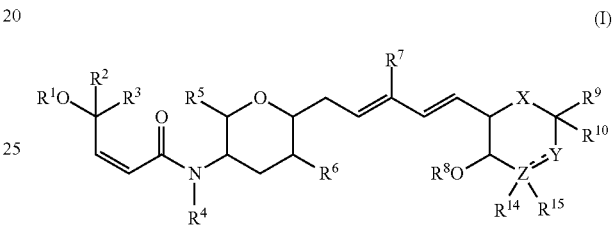

(I)

wherein:
X is selected from the group consisting of O and $C(R^{11})_2$;
Y is selected from the group consisting of C, CH, $C(R^{11})_2$ and O;
Z is selected from the group consisting of C and CH;
⫽ represents a single or a double bond between Y and Z;

$R^1$ is selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$,
  wherein $R^{11}$ is H, $C_{1-6}$-alkyl, or halo($C_{1-6}$-alkyl),
  each Pg is independently a hydroxy protecting group, and
  wherein $R^{12}$ and $R^{13}$ are independently selected from the group consisting of H, $C_{1-6}$-alkyl, and halo($C_{1-6}$-alkyl);
  or $R^{12}$ and $R^{13}$, together with the nitrogen atom to which they are bound, form a heterocyclic or heteroaromatic ring;
$R^2$, $R^3$, $R^4$, $R^5$, and $R^6$ are independently selected from the group consisting of H, $C_{1-6}$-alkyl, and halo($C_{1-6}$-alkyl);
$R^7$ is selected from the group consisting of H, $C_{1-6}$-alkyl and halo($C_{1-6}$-alkyl);
$R^9$ and $R^{10}$ are independently selected from the group consisting of H, $C_{1-6}$-alkyl, and $C_{1-6}$-alkyl substituted with one to three groups independently selected from halo, hydroxy, and $C_{1-6}$-alkoxy;

or $R^9$ and $R^{10}$, together with the carbon atom to which they are bound, form a carbonyl group; and wherein $R^8$, $R^{14}$, and $R^{15}$ are defined by (A), (B), or (C):

(A) $R^8$ is a substituted polyethylene glycol-: moiety represented by the formula (IV')

$$R^{21}\diagdown\diagdown[O\diagdown]_n\text{-}\text{-}\text{-}\qquad(IV')$$

wherein:
 $R^{21}$ is selected from the group consisting of azide, tetrazole and triazole with hydrogen, alkyl, or substituted alkyl substituents; and
 n is an integer selected from 1, 2, 3, 4, 5, and 6; and
 $R^{14}$ and $R^{15}$ are independently selected from the group consisting of hydrogen, halo($C_{1\text{-}6}$-alkyl), $C(O)R^{11}$, F, Cl, $NO_2$, and $B(OR^{11})_2$, wherein at least one of $R^{14}$ and $R^{15}$ is other than hydrogen when ⫻ represents a single bond, and wherein $R^{11}$ is as defined above;
 or $R^{14}$ and $R^{15}$, together with the carbon atom to which they are bound, form an epoxide ring or a carbonyl group;
 or $R^{14}$ and $R^{15}$ together represent a substituent selected from the group consisting of =$NHNH_2$ and =NHOH; or (B) $R^8$, $R^{14}$, and $R^{15}$ together with the carbon atoms to which they are bound, represent the following structure:

[structure]

or (C) $R^8$ is H and
 $R^{14}$ and $R^{15}$, together with the carbon atom to which they are bound, form a carbonyl group; or
 $R^{14}$ and $R^{15}$ together represent a substituent selected from the group consisting of =$NHNH_2$ and =NHOH.

2. The compound according to claim 1 having Formula (Ia):

[structure (Ia)]

wherein:
 $R^8$ is the polyethylene glycol moiety of formula (IV')
 $R^9$ and $R^{10}$ are independently selected from the group consisting of H, $C_{1\text{-}6}$-alkyl, and $C_{1\text{-}6}$-alkyl substituted with one to three groups independently selected from halo, hydroxy, and $C_{1\text{-}6}$-alkoxy; and $R^{14}$ and $R^{15}$ are independently selected from the group consisting of hydrogen, halo($C_{1\text{-}6}$-alkyl), $C(O)R^{11}$, F, Cl, $NO_2$, and $B(OR^{11})_2$, wherein at least one of $R^{14}$ and $R^{15}$ is other than hydrogen;

or $R^{14}$ and $R^{15}$, together with the carbon atom to which they are bound, form an epoxide ring or a carbonyl group.

3. The compound according to claim 2 having Formula Ib:

[structure (Ib)]

4. The compound according to claim 3, wherein $R^1$ is $C(O)R^{11}$ and $R^{11}$ is $C_{1\text{-}6}$-alkyl or halo($C_{1\text{-}6}$-alkyl).

5. The compound according to claim 4, wherein $R^1$ is $C(O)CH_3$.

6. The compound according to claim 3, wherein at least one of $R^2$, $R^3$, $R^5$, and $R^6$ is $C_{1\text{-}6}$-alkyl.

7. The compound according to claim 6, wherein at least one of $R^2$, $R^3$, $R^5$, and $R^6$ is $CH_3$.

8. The compound according to claim 3, wherein $R^4$ is hydrogen.

9. The compound according to claim 3, wherein $R^7$ is $CH_3$ or $CF_3$.

10. The compound according to claim 3, wherein at least one of $R^9$ and $R^{10}$ is selected from the group consisting of $C_{1\text{-}6}$-alkyl and $C_{1\text{-}6}$-alkyl substituted with one to three groups independently selected from halo, hydroxy, and $C_{1\text{-}6}$-alkoxy.

11. The compound according to claim 10, wherein at least one of $R^9$ and $R^{10}$ is selected from the group consisting of $CH_3$, $CH_2I$, and $CH_2OH$.

12. The compound according to claim 1, wherein $R^8$, $R^{14}$, and $R^{15}$ together with the carbon atoms to which they are bound, represent the following structure:

[structure]

13. The compound according to claim 1, wherein $R^1$ is $C(O)R^{11}$ and $R^{11}$ is $C_{1\text{-}6}$-alkyl or halo($C_{1\text{-}6}$-alkyl).

14. The compound according to claim 1, wherein at least one of $R^2$, $R^3$, $R^5$, and $R^6$ is $C_{1\text{-}6}$-alkyl.

15. The compound according to claim 1, wherein $R^4$ is hydrogen.

16. The compound according to claim 1, wherein $R^7$ is $CH_3$ or $CF_3$.

17. The compound according to claim 2 having Formula (Ic) or Formula (Id):

(Ic)

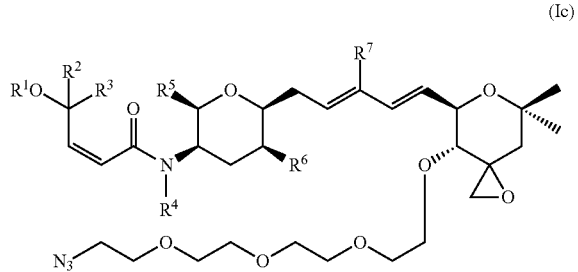

(Id)

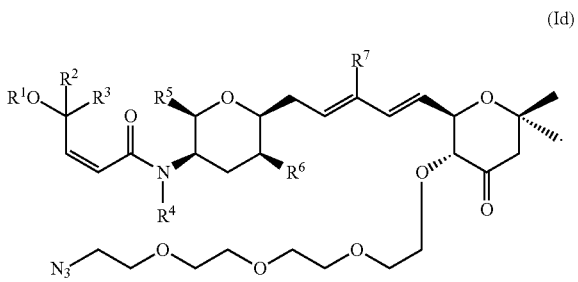

18. The compound according to claim 17, wherein $R^1$ is $C(O)R^{11}$ and $R^{11}$ is $C_{1-6}$-alkyl or halo($C_{1-6}$-alkyl).

19. The compound according to claim 18, wherein $R^1$ is $C(O)CH_3$.

20. The compound according to claim 17, wherein at least one of $R^2$, $R^3$, $R^5$, and $R^6$ is $C_{1-6}$-alkyl.

21. The compound according to claim 20, wherein at least one of $R^2$, $R^3$, $R^5$, and $R^6$ is $CH_3$.

22. The compound according to claim 17, wherein $R^4$ is hydrogen.

23. The compound according to claim 17, wherein $R^7$ is $CH_3$ or $CF_3$.

24. The compound according to claim 2 selected from the group consisting of:

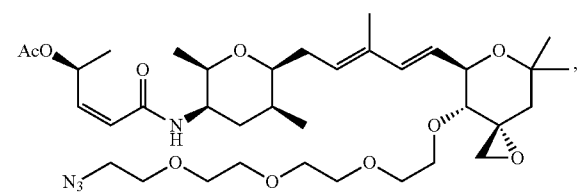

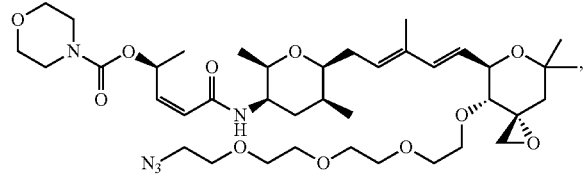

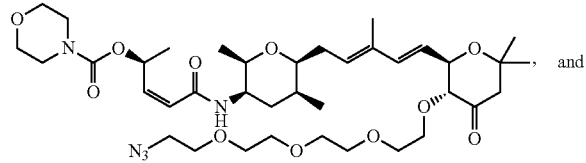, and

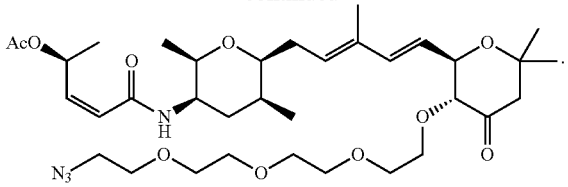

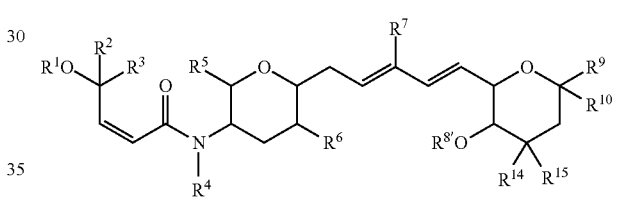

25. A pharmaceutical composition comprising a compound according to claim 1, a stereoisomer, or pharmaceutically acceptable salt or ester thereof and a pharmaceutically acceptable carrier.

26. A method for treating a disorder in a subject suffering therefrom, comprising administering to the subject a therapeutically effective amount of a compound according to claim 1, or a stereoisomer, pharmaceutically acceptable salt or ester thereof, wherein the disorder is selected from the group consisting breast adenocarcinoma, nonsmall cell lung cancer, head cancer, neck cancer, colon cancer, kidney cancer and combinations thereof.

27. A process for preparing a compound, stereoisomer, or pharmaceutically acceptable salt or ester thereof having Formula (Ia):

(Ia)

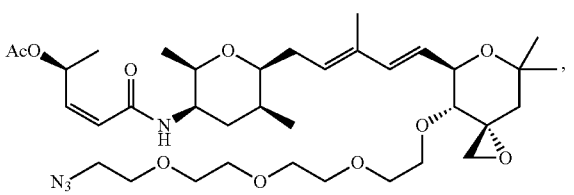

wherein:

$R^1$ is selected from the group consisting of H, Pg, $C_{1-6}$-alkyl, halo($C_{1-6}$-alkyl), $C(O)R^{11}$, $C(O)OR^{11}$, and $C(O)^{12}R^{13}$, wherein each $R^{11}$ is independently H, $C_{1-6}$-alkyl, or halo($C_{1-6}$-alkyl), and wherein $R^{12}$ and $R^{13}$ are independently selected from the group consisting of H, $C_{1-6}$-alkyl, and halo($C_{1-6}$-alkyl);

or $R^{12}$ and $R^{13}$, together with the nitrogen atom to which they are bound, form a heterocyclic or heteroaromatic ring;

$R^2$, $R^3$, $R^4$, $R^5$, and $R^6$ are independently selected from the group consisting of H, $C_{1-6}$-alkyl, and halo($C_{1-6}$-alkyl);

$R^7$ is selected from the group consisting of H, $C_{1-6}$-alkyl and halo($C_{1-6}$-alkyl); and $R^8$ is a substituted polyethylene glycol moiety, and $R^9$ and $R^{10}$ are independently selected from the group consisting of H, $C_{1-6}$-alkyl, and $C_{1-6}$-alkyl substituted with one to three groups independently selected from halo, hydroxy, $C_{1-6}$-alkoxy, and OPg;

$R^{14}$ or $R^{15}$ are independently selected from the group consisting of hydrogen, halo($C_{1-6}$-alkyl), $C(O)R^{11}$, F, Cl, $NO_2$, and $B(OR^{11})_2$, wherein at least one of $R^{14}$ and $R^{15}$ is other than hydrogen, and wherein $R^{11}$ is as defined above; and each Pg is independently a hydroxy protecting group;

said method comprising the steps of:
(A) contacting a compound of Formula (III):

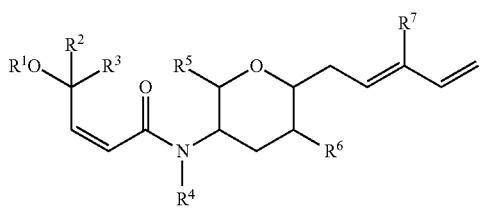

(III)

wherein $R^1$, $R^2$, $R^3$, $R^4$, $R^5$, $R^6$, and $R^7$ are as defined above, with a compound of Formula (IIa):

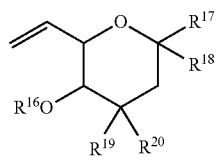

(IIa)

wherein $R^{16}$ is hydrogen and $R^{17}$, $R^{18}$, $R^{19}$, and $R^{20}$ are as defined above, in the presence of an olefin metathesis catalyst; and
(B) contacting the product of step (A) with a compound of the formula (IV)

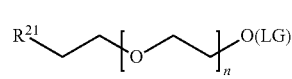

(IV)

wherein:
$R^{21}$ is selected from the group consisting of azide, tetrazole and triazole with hydrogen, alkyl, or substituted alkyl substituents;
n is an integer selected from 1, 2, 3, 4, 5, and 6; and
LG is a leaving group.

* * * * *